US009512712B2

United States Patent
Donderici et al.

(10) Patent No.: US 9,512,712 B2
(45) Date of Patent: Dec. 6, 2016

(54) METHODS OF DEEP AZIMUTHAL INSPECTION OF WELLBORE PIPES

(71) Applicant: Halliburton Energy Services, Inc., Houston, TX (US)

(72) Inventors: Burkay Donderici, Houston, TX (US); Luis Sanmartin, Houston, TX (US); Reza Khalaj Amineh, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/888,753

(22) PCT Filed: Jun. 25, 2015

(86) PCT No.: PCT/US2015/037665
§ 371 (c)(1),
(2) Date: Nov. 3, 2015

(87) PCT Pub. No.: WO2016/007307
PCT Pub. Date: Jan. 14, 2016

(65) Prior Publication Data
US 2016/0160629 A1   Jun. 9, 2016

Related U.S. Application Data

(60) Provisional application No. 62/023,524, filed on Jul. 11, 2014.

(51) Int. Cl.
*G01N 27/90* (2006.01)
*E21B 47/00* (2012.01)

(52) U.S. Cl.
CPC .......... *E21B 47/0006* (2013.01); *E21B 47/00* (2013.01); *G01N 27/9046* (2013.01)

(58) Field of Classification Search
CPC ... G01N 27/9046; E21B 47/0006; E21B 47/00
(Continued)

(56) References Cited

U.S. PATENT DOCUMENTS 2,790,140 A * 4/1957 Bender .............. G01N 27/9033
324/220
3,209,243 A * 9/1965 Walters ................. E21B 47/082
324/220
(Continued)

FOREIGN PATENT DOCUMENTS

WO   2014105080 A1   7/2014
WO   2016007307 A1   1/2016

OTHER PUBLICATIONS

Magnetic Thickness Tool, Company: GE Energy-GE, Tool: Sondex Wireline Tools—Cased Hole Products, 2003.
(Continued)

*Primary Examiner* — Jay Patidar
(74) *Attorney, Agent, or Firm* — McDermott Will & Emery LLP; Scott Richardson

(57) ABSTRACT

Methods including conveying a pipe inspection tool into a wellbore having at least a first pipe positioned within a second pipe, the pipe inspection tool including an electromagnetic sensor. A first excitation signal is transmitted from a first x-coil of the electromagnetic sensor, and a first response signal derived from the first excitation signal is received at the first x-coil or a second x-coil of the electromagnetic sensor. A second excitation signal is then transmitted from a first y-coil of the electromagnetic sensor, and a second response signal derived from the second excitation signal is received at the first y-coil or a second y-coil of the electromagnetic sensor. The first and second response signals are then compared to determine an azimuthal characteristic of the second pipe.

17 Claims, 10 Drawing Sheets

(58) Field of Classification Search
USPC ... 324/220–221, 238; 73/152.57; 166/250.05
See application file for complete search history.

(56) References Cited

U.S. PATENT DOCUMENTS

| | | | |
|---|---|---|---|
| 4,292,589 A | 9/1981 | Bonner | |
| 5,049,817 A * | 9/1991 | Cecco | G01N 27/904 324/220 |
| 5,461,313 A | 10/1995 | Bohon et al. | |
| 5,581,037 A | 12/1996 | Kwun et al. | |
| 6,281,678 B1 * | 8/2001 | Auville | G01N 27/902 324/220 |
| 7,560,920 B1 | 7/2009 | Ouyang et al. | |
| 8,471,562 B2 | 6/2013 | Knizhnik | |
| 8,823,369 B2 * | 9/2014 | Segletes | G01N 27/84 324/216 |
| 2009/0195244 A1 | 8/2009 | Mouget et al. | |
| 2009/0242200 A1 | 10/2009 | Badoux et al. | |
| 2012/0095686 A1 | 4/2012 | Legendre et al. | |

OTHER PUBLICATIONS

Haugland, S.M., Fundamental Analysis of the Remote-Field Eddy-Current Effect, IEEE Transactions on Magnetics, vol. 32, No. 4, 1996.
Al-Yateem, et al., Measuring and Profiling Casing Corrosion for Predicting Subsurface Leaks, IPTC 17170, 2013.
Brill, et al., Electromagnetic Casing Inspection Tool for Corrosion Evaluation, IPTC 14865, 2012.
Arbuzov et al., Memory Magnetic Imaging Defectoscopy, SPE 162054, 2012.
Garcia, et al., Successful Application of a New Electromagnetic Corrosion Tool for Well Integrity Evaluation in Old Wells Completed with Reduced Diameter Tubular, IPTC 16997, 2013.
International Search Report and Written Opinion for PCT/US2015/037665 dated Sep. 18, 2015.

\* cited by examiner

METHODS OF DEEP AZIMUTHAL INSPECTION OF WELLBORE PIPES

CROSS-REFERENCE TO RELATED APPLICATIONS

This application is a National Stage entry of and claims priority to International Application No. PCT/US2015/037665, filed on Jun. 25, 2015, which claims priority to U.S. Provisional Patent App. Ser. No. 62/023,524, filed on Jul. 11, 2014.

BACKGROUND

Wellbores in the oil and gas industry are typically drilled using a drill string with a drill bit secured to its distal end. The drilled wellbore is subsequently completed by cementing a string of metal pipes connected end-to-end within the wellbore. Commonly called "casing," such strings of metal pipes increase the structural stability of the wellbore and provide a flow path between the earth's surface and selected subterranean formations. Moreover, in some wellbores, one or more production pipes are extended into the wellbore to provide a conduit for hydrocarbons to be conveyed to the earth's surface. Accordingly, as used herein, the term "pipe" or "wellbore pipe" will refer to metal pipes or pipelines that line the walls of a wellbore, such as casing, and also production pipes extended into a wellbore to facilitate hydrocarbon production operations.

During the lifetime of a well, wellbore pipes are exposed to high volumes of materials and fluids required to pass through them, including chemically aggressive fluids. In harsh environments, however, the pipes may be subject to corrosion that may affect their functionality. Timely and accurate detection of structural integrity problems such as cracks, pinholes, and corrosion is essential to reducing costs associated with wellbore intervention, since pulling wellbore pipes, such as casing, out of a wellbore for further inspection and repairs and replacing can be a very expensive task.

Some wellbores include multiple concentric pipes or strings of casing secured within the wellbore with an innermost pipe that exhibits a relatively narrow diameter. As will be appreciated, the diameter of the innermost pipe limits the size of the monitoring and intervention system that can be deployed to monitor the integrity of all of the concentric pipes. With multiple concentric pipes, another problem is the ability to effectively monitor the outermost pipes from the innermost pipe, since any monitoring system has to be able to sense through a number of pipe layers, each of which may have developed distinct problems or defects.

Several different sensing methods have been proposed for detecting corrosion and other types of defects in pipelines, some of which have been applied to wellbore pipes used for extracting hydrocarbons. The most common method utilizes acoustic wave pulses and analysis of reflections from the surface of a pipe wall to image any defects. Electromagnetic inspection methods are also used for the same purpose, and are desirable since they allow an operator to sense beyond the first pipe, and thereby obtain measurements from second, third, or additional pipes beyond the third pipe. Existing pipe inspection methods, however, are either azimuthally sensitive and shallow or azimuthally insensitive and deep.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to maintenance of wellbores in the oil and gas industry and, more particularly, to monitoring and evaluating corrosion and defects in wellbore pipes.

Embodiments of the present disclosure provide improved electromagnetic inspection methods for wellbore pipes, such as concentric strings of casing or production tubing positioned within a wellbore. The presently described methods generally rely on X- or Y-oriented coil antennas. As compared to conventional coil antennas and conventional electromagnetic inspection methods, the exemplary coil antennas of the present disclosure and related methods can provide azimuthal sensing of wellbore pipes that lie radially beyond the first or innermost wellbore pipe, that is, the ability to sense second, third, and further wellbore pipes concentrically arranged about the first wellbore pipe. Some embodiments described herein use separated X- and Y-coil antennas that can simultaneously sense deep and shallow pipe features and provide azimuthal information about pipe features that are beyond the first wellbore pipe. Moreover, the embodiments described herein help facilitate measurement of azimuthal distribution of defects on wellbore pipes as opposed to the volumetric approach of conventional coil antennas.

Figure 1:
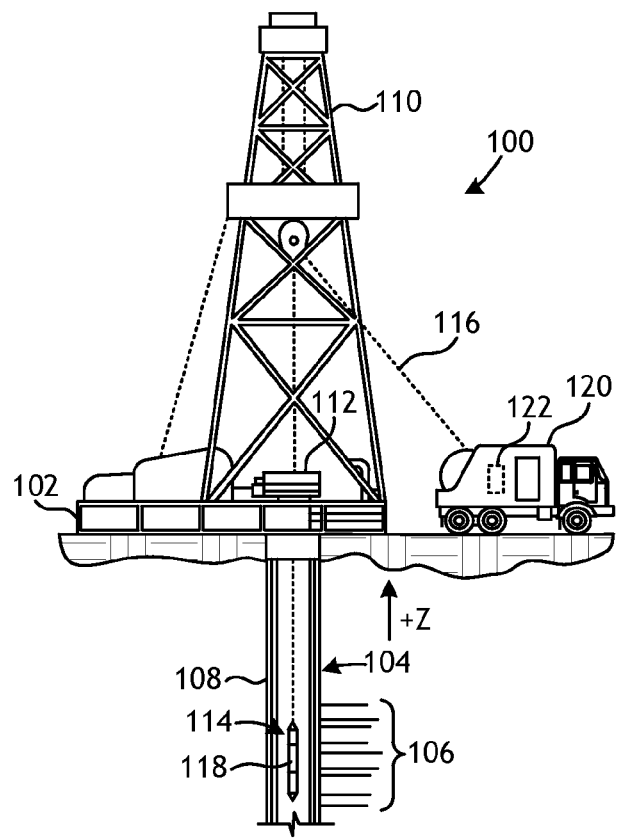
FIG. 1 is a schematic diagram of an exemplary wireline system that may employ the principles of the present disclosure.

FIG. 1 is a schematic diagram of an exemplary wireline system 100 that may employ the principles of the present disclosure, according to one or more embodiments. As illustrated, the wireline system 100 may include a surface platform 102 positioned at the earth's surface and a wellbore 104 that extends from the surface platform 102 into one or more subterranean formations 106. In other embodiments, such as in offshore operations, a volume of water may separate the surface platform 102 and the wellbore 104. The wellbore 104 may be lined with one or more pipes 108, also referred to as strings of casing. In some embodiments, portions of the wellbore 104 may have only one pipe 108 positioned therein, but other portions of the wellbore 104 may be lined with two or more concentrically-disposed pipes 108. The pipes 108 may be made of plain carbon steel, stainless steel, or another material capable of withstanding a variety of forces, such as collapse, burst, and tensile failure.

The wireline system 100 may include a derrick 110 supported by the surface platform 102 and a wellhead installation 112 positioned at the top of the wellbore 104. A pipe inspection tool 114 may be suspended into the wellbore 104 on a cable 116. In some embodiments, the pipe inspection tool 114 may alternatively be suspended within a production pipe (not shown) positioned within the pipes 108 that line the wellbore 104 (i.e., casing). In such embodiments, the production pipe may extend by itself within the pipes 108 or alternatively be positioned adjacent one or more eccentrically-located production pipes that are also positioned within the pipes 108. Accordingly, as used herein, "pipes 108" may refer to strings of casing that line the wellbore 104 and/or at least one production pipe extended into the wellbore 104.

The pipe inspection tool 114 may comprise an electromagnetic, non-destructive inspection tool. Its operation may be based on either the flux-leakage principle or the eddy-current principle, or a combination thereof, and may be insensitive to non-magnetic deposits and is operable irrespective of the nature of the fluid mixture flowing into/out of the wellbore 104. The pipe inspection tool 114 can be used for the detection of localized damage or defects in the pipes 108. In operation, the pipes 108 are subjected to a strong primary magnetic field produced by the pipe inspection tool 114 and, due to their ferromagnetic nature, eddy currents will be generated inside the pipes. These eddy currents produce secondary magnetic fields that are measured along with the primary magnetic field with the tool 114. In the presence of discontinuities or defects in the metal of the pipes 108, such as pits and holes caused by corrosion, the changes in the secondary magnetic field can be detected with the pipe inspection tool 114.

To accomplish this, the pipe inspection tool 114 may include one or more electromagnetic sensors 118, which may be communicably coupled to the cable 116. The cable 116 may include conductors for conveying power to the pipe inspection tool 114 and also for facilitating communication between the surface platform 102 and the pipe inspection tool 114. A logging facility 120, shown in FIG. 1 as a truck, may collect measurements from the electromagnetic sensors 118, and may include computing facilities 122 for controlling, processing, storing, and/or visualizing the measurements gathered by the electromagnetic sensors 118. The computing facilities 122 may be communicably coupled to the pipe inspection tool 114 by way of the cable 116.

The electromagnetic sensors 118 may include one or more electromagnetic coil antennas that may be used as transmitters, receivers, or a combination of both (i.e., transceivers) for obtaining in situ measurements of the pipe(s) 108 and thereby determining the structural integrity or condition of each pipe 108. Multiple measurements may be made by the electromagnetic sensors 118 as the pipe inspection tool 114 is lowered into the wellbore 104 (i.e., "down log") and/or raised back to the surface of the well (i.e., "up log"). Each measurement gives an indication of the condition of the pipes 108 at the specific depth where the pipe inspection tool 114 is located.

The principle of measurement is based on two separate mechanisms: magnetic fields that follow the magnetically shortest path (such as in magnetic circuits) and eddy currents that are induced on the pipes 108, which create signals as a function of the electromagnetic skin depth of the pipes 108. Received signals are also affected by casing collars and natural changes in the magnetic properties of different pieces of a wellbore pipe. After received signals are recorded, they are interpreted by an algorithm, and features of the pipes 108 can be calculated from the measurements. These calculations and determinations can be undertaken, for example, using the computing facilities 122 at the logging facility 120. Advantageously, electromagnetic inspection tools, such as the pipe inspection tool 114, provide a capability to make measurements of the pipes 108 beyond the first or innermost wellbore pipe.

In some embodiments, the electromagnetic sensors 118 may be designed to operate in a centralized position within the innermost pipe 108, such as through the use of one or more centralizers (not shown) attached to the body of the pipe inspection tool 114. In other embodiments, however, the electromagnetic sensors 118 may be designed to be adjacent or in intimate contact with the inner wall of the innermost pipe 108. In such embodiments, the electromagnetic sensors 118 may be mounted on one or more deployable sensor pads (not shown) positioned on actuatable arms (not shown) that move the electromagnetic sensors 118 radially outward toward the inner wall of the innermost pipe 108.

Figure 2:
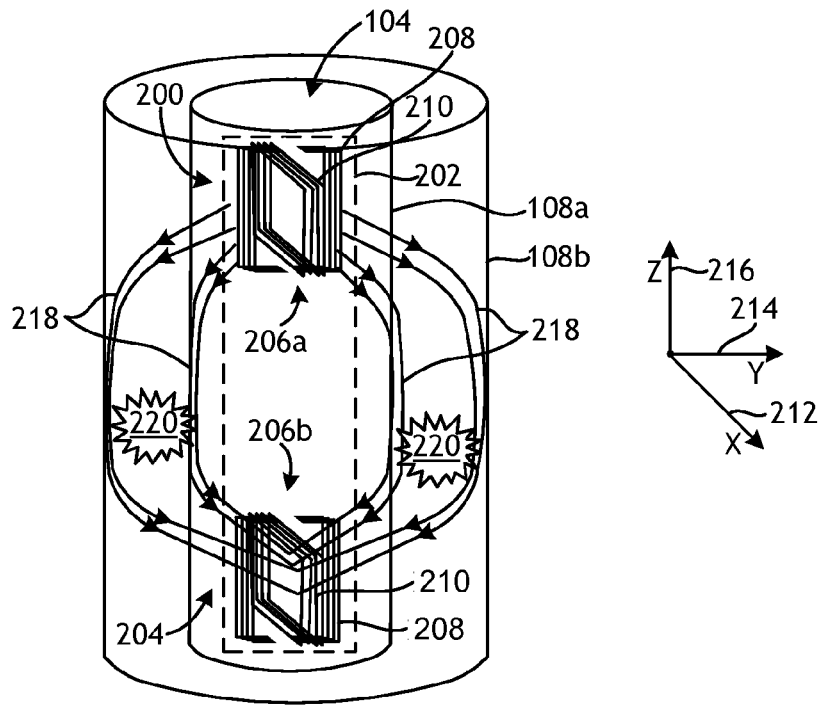
FIG. 2 is a schematic side view of an exemplary pipe inspection tool.

FIG. 2 is a schematic side view of an exemplary pipe inspection tool 200, according to one or more embodiments. The pipe inspection tool 200 may be similar to or the same as the pipe inspection tool 114 of FIG. 1 and, therefore, may be used to monitor the pipes 108 positioned within the wellbore 104. In the illustrated embodiment, the pipes 108 are shown as a first pipe 108a and a second pipe 108b, where the first pipe 108a is the innermost wellbore pipe and is located within the second pipe 108b. In some embodiments, the first and second pipes 108a,b may line the walls of the wellbore 104 as concentric strings of casing or liner. In other embodiments, however, the first pipe 108a may comprise a production pipe concentrically- or eccentrically-positioned within the second pipe 108b, which may comprise casing that lines the wellbore 104, without departing from the scope of the disclosure. As will be appreciated, more than two pipes 108a,b may be used in any of the embodiments described herein.

As illustrated, the pipe inspection tool 200 includes a body 202 and at least one electromagnetic sensor 204 positioned within or otherwise attached to the body 202. The electromagnetic sensor 204 may be similar to or the same as the electromagnetic sensor 118 of FIG. 1. In the illustrated embodiment, the electromagnetic sensor 204 may include a transmitter antenna 206a and a receiver antenna 206b axially spaced from the transmitter antenna 206a. Each of the transmitter and receiver antennas 206a,b may include at least an x-coil 208 and a y-coil 210 collocated with each other. While not expressly shown in FIG. 2, the transmitter and receiver antennas 206a,b may each include a bobbin or core about which the x- and y-coils 208, 210 are wound. The core may be made of a magnetically-permeable material and may help amplify or boost electromagnetic signals emitted by the transmitter antenna 206a. It is noted that, while the x- and y-coils 208, 210 are depicted in FIG. 2 as comprising a number of disconnected rectangular windings, such is for illustration purposes only. Rather, the windings can be of any shape other than rectangle, and the windings may be connected to each other in helical form.

The x-coil 208 may be wrapped about the core in a first direction 212, and the y-coil 210 may be wrapped about the core in a second direction 214, where the second direction 214 is orthogonal to the first direction 212. Accordingly, the first direction 212 may constitute the x-direction with respect to the wellbore 104 and the second direction 214 may constitute the y-direction with respect to the wellbore 104, which is 90° offset from the first direction 212. A central axis of the pipe inspection tool 200 may extend in a third direction 216 orthogonal to both the first and second directions 212, 214 and otherwise parallel to the longitudinal axis of the wellbore 104. Accordingly, the third direction 216 may constitute the z-direction with respect to the wellbore 104 and may be 90° offset from both the first and second directions 212, 214.

Upon exciting the x- and y-coils 208, 210, such as through the influx of an alternating current or a voltage, the transmitter antenna 206a may generate magnetic fields 218 that extend radially away from the pipe inspection tool 200 and penetrate at least one of the pipes 108a,b. The magnetic fields 218 may be subsequently received by the receiver antenna 206b. Each of the x- and y-coils 208, 210 may generate magnetic fields 218 in mutually orthogonal directions. In the illustrated embodiment, however, and for purposes of clarity, only magnetic fields 218 emanating from the x-coil 208 are depicted, but it will be appreciated that the y-coil 210 may equally emit magnetic fields that are angularly offset from the depicted magnetic fields 218 by about 90°.

A horizontally-oriented magnetic dipole generates alternating magnetic fields 218, which are normal to the surface area of the transmitter antenna 206a. These magnetic fields 218 circulate around the pipes 108a,b and come back to complete the circuit on the other side of the transmitter antenna 206a. The magnetic fields 218 take various paths to complete the circuit. Due to the relatively high magnetic permeability of the pipes 108a,b, the magnetic fields 218 prefer taking the paths that are on the pipes 108a,b more than elsewhere. One short path is the one that azimuthally and/or laterally traverses the pipes 108a,b. Since this path is far from the receiver antenna 206b, it does not contribute to the received signal. As shown in FIG. 2, however, another path is completed as the magnetic fields 218 move vertically down the pipes 108a,b and complete the circuit through the receiver antenna 206b.

Due to the axial nature of the magnetic fields 218 on the pipes 108a,b, any horizontally-oriented defect 220 (two shown) impedes the flow of the magnetic fields 218 and creates a disturbance that may be detected at the receiver antenna 206b. The defects 220 may include, for example, corrosion, fractures, holes, cracks, and decreased wall thickness in the pipes 108a,b. This type of detection mostly utilizes the fact that the pipes 108a,b exhibit a magnetic permeability different from that of air, which is true for most tubular wellbore pipes used in the oil and gas industry. The only application this approach would be less applicable to may be one that utilizes pipes 108a,b made of chrome, for instance.

In the case of electric fields (not depicted in FIG. 2), the electric fields that are induced by the alternating magnetic fields 218 travel axially on the pipes 108a,b and they close a circuit around each pipe 108a,b. Due to the axial nature of electric field flow on the pipes 108a,b, this type of method is also mostly sensitive to defects 220 in the form of horizontal cracks, since such defects 220 impede the flow of the electric fields. This approach is sensitive to both conductivity and magnetic permeability of the pipes 108a,b since the resistance of the pipe 108a,b is a function of both. In particular, conductivity directly determines the resistance of the pipe 108a,b while magnetic permeability is only affected through changes in the skin depth of the pipes 108a,b. When skin depth on the pipes 108a,b is small, effective electrical thickness of the pipes 108a,b decreases and resistance per length of the pipes 108a,b increases. When the skin depth on the pipes 108a,b is large, however, the effective electrical thickness of the pipes 108a,b increases and the resistance per length of the pipes 108a,b decreases.

In operation of the pipe inspection tool 200, and any of the pipe inspection tools described herein, both electrical and magnetic sensing mechanisms may be in place simultaneously and the received signals may be affected by both. Due to complicated physics, numerical interpretation models are usually preferred to analyze the received response signals as opposed to those based on analytical formulas.

Figure 3:
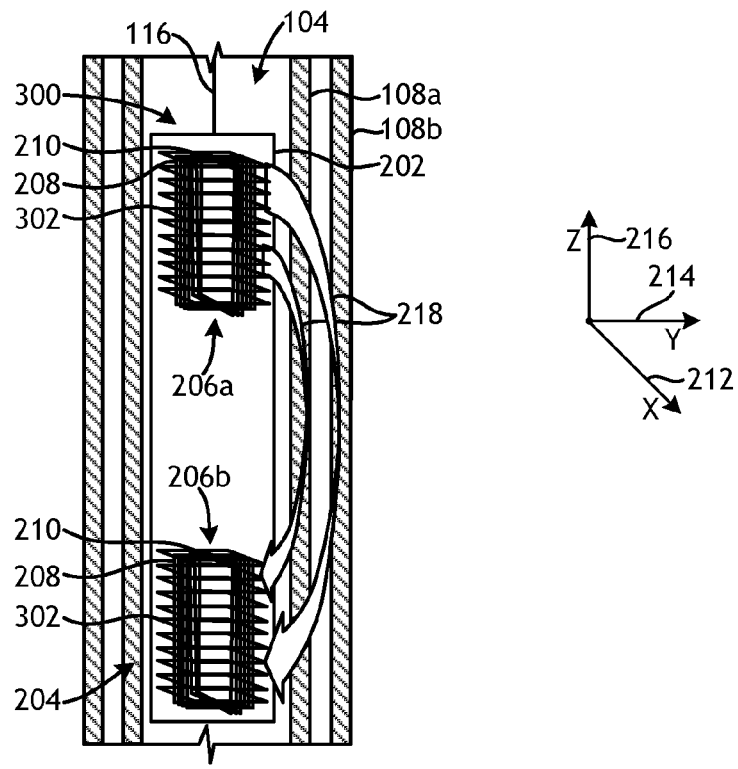
FIG. 3 is a partial cross-sectional side view of another exemplary pipe inspection tool.

FIG. 3 is a partial cross-sectional side view of another exemplary pipe inspection tool 300, according to one or more embodiments. The pipe inspection tool 300 may be similar in some respects to the pipe inspection tool 200 of FIG. 2 and therefore may be best understood with reference thereto, where like numerals correspond to like elements or components not described again in detail. Similar to the pipe inspection tool 200, the pipe inspection tool 300 may be used to monitor the pipes 108a,b of the wellbore 104. Moreover, the pipe inspection tool 300 may include the body 202 and the electromagnetic sensor 204 positioned within the body 202, where the electromagnetic sensor 204 includes the transmitter antenna 206a and the receiver antenna 206b axially spaced from the transmitter antenna 206a.

Unlike the pipe inspection tool 200 of FIG. 2, however, the transmitter and receiver antennas 206a,b may each further include a z-coil 302 collocated with the x- and y-coils 208, 210 and also wrapped about corresponding cores (not expressly shown) of each antenna 206a,b. Each z-coil 302 may comprise a continuous solenoid or helical winding pattern that extends longitudinally between the axial upper and lower ends of the corresponding transmitter and receiver antennas 206a,b. While depicted in FIG. 3 as exhibiting a generally square-shape or polygonal profile, the z-coil 302 may alternatively exhibit a circular or elliptical shape, without departing from the scope of the disclosure.

The z-coil 302 may be wrapped about the core in the third direction 216, which, as mentioned above, is orthogonal to both the first and second directions 212, 214. Accordingly, the transmitter and receiver antennas 206a,b may each provide three collocated coil antennas. In some embodiments, the z-coil 302 may be wound first on the core, and the x- and y-coils 208, 210 may be subsequently around the z-coil 302, although the scope of the disclosure is not limited to this configuration. Upon exciting the z-coil 302, such as through the influx of an alternating current or a voltage, the transmitter antenna 206a may generate magnetic fields 218 that extend radially away from the pipe inspection tool 200 in substantially the third direction 216 to penetrate at least one of the pipes 108a,b. Each of the x-, y-, and z-coils 208, 210, 302 may generate magnetic fields 218 in mutually orthogonal directions, which may subsequently be received by the receiver antenna 206b. More particularly, the x-coil 208 produces magnetic fields 218 of a spatially distributed X magnetic dipole, the y-coil 210 produces magnetic fields 218 of a spatially distributed Y magnetic dipole, and the z-coil 302 produces magnetic fields 218 of a spatially distributed Z magnetic dipole.

The depth of investigation in eddy current methods is dependent on several factors, the most important being the distance (axial separation) between the transmitter and receiver antennas 206a,b. The longer the distance between the transmitter and receiver antennas 206a,b, the more electric or magnetic fields 218 can travel away from the pipe inspection tool 200 before they complete the circuit. Since magnetic fields 218 and currents always take the shortest path (magnetically and electrically), depth of investigation is also dependent upon the properties of the pipes 108a,b that are involved. For example, if the first or innermost pipe 108a is highly magnetically-permeable, most of the magnetic fields 218 will flow on the innermost pipe 108a, and less will flow to any wellbore pipes radially offset from the innermost pipe 108a. In the case where there is increased axial separation between the transmitter and receiver antennas 206a,b, more flow of the magnetic fields 218 may be obtained in the second pipe 108b or any wellbore pipes radially beyond the first pipe 108a.

In time-domain systems, where a measurement is made as a function of time, received signals at the receiver antenna 206b at early times are only sensitive to wellbore pipes that are shallow (i.e., radially close to the pipe inspection tool), where received signals that are "late time" are sensitive to both shallow and deep pipes (i.e., radially close and far from the pipe inspection tool). In frequency-domain systems, where steady state discrete frequency measurements are made, high frequencies (typically 10-1000 Hz or 1-100 ms) are sensitive to shallow pipe features, while low frequencies (typically 0.1-10 Hz or 100-10000 ms) are sensitive to deep pipe features. The optimum frequency range to sense a particular wellbore pipe depends on the effective distance between the transmitter and receiver antennas 206a,b and the properties of the pipes that come before the target pipe as electromagnetic waves penetrate them. For example, more conductive and magnetically permeable pipes require lower frequencies (or equivalently later times for time-domain systems), while less conductive and magnetically permeable pipes require higher frequencies (or equivalently earlier times for time-domain systems).

Figure 4A:
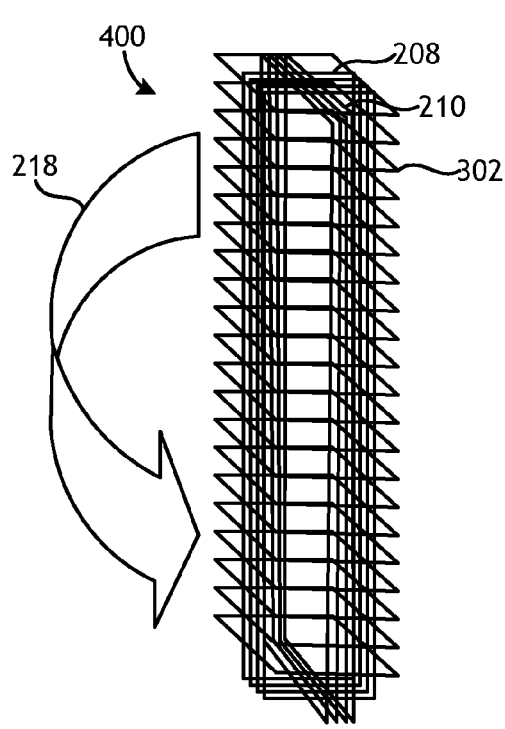
FIGS. 4A and 4B depict schematic diagrams of a transceiver antenna and separate transmitter and receiver antennas, respectively.
Figure 4B:
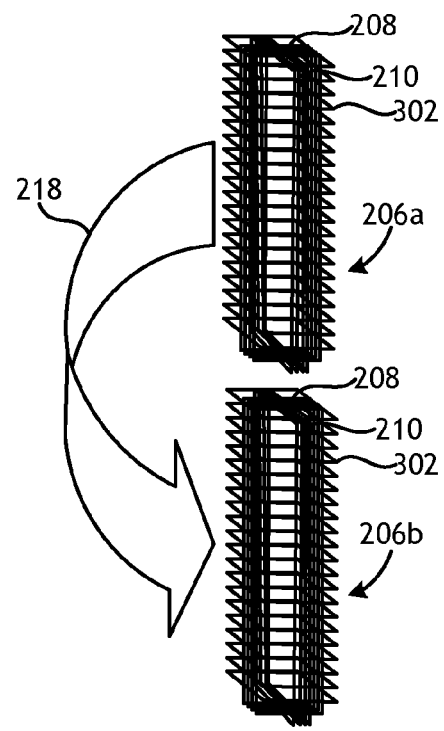

FIGS. 4A and 4B depict schematic diagrams of a transceiver antenna 400 and separate transmitter and receiver antennas 206a,b, respectively. The transceiver antenna 400 of FIG. 4A may be similar in some respects to each of the transmitter and receiver antennas 206a,b and may, therefore, include x-, y-, and z-coils 208, 210, 302 that generate magnetic fields 218 in mutually orthogonal directions (only one direction shown). Unlike the transmitter and receiver antennas 206a,b of FIG. 4B, however, the transceiver antenna 400 may be used as both a transmitter antenna and a receiver antenna. In cases where the transmitter and receiver antennas are collocated, or where only a single antenna exists for both transmitting and receiving, as in the case of the transceiver antenna 400, the depth of investigation is effectively proportional to the length of the transceiver antenna 400. An alternative implementation of the embodiment in FIG. 4A is one where the transmitter and receiver antennas are separate coils but they are collocated axially and with different sizes in the radial direction. This alternative implementation has advantages since the transmitting and receiving circuitry are decoupled and direct signal component and any transmitter ringing effects may then be minimized. As used herein, the term "ringing effect" refers to a condition where transmitter excitation remains around the transmitter coil even after the excitation is terminated due to electromagnetic interactions with electromagnetic scatterers around the transmitter, including the transmitter coil wire itself.

Figure 5A:
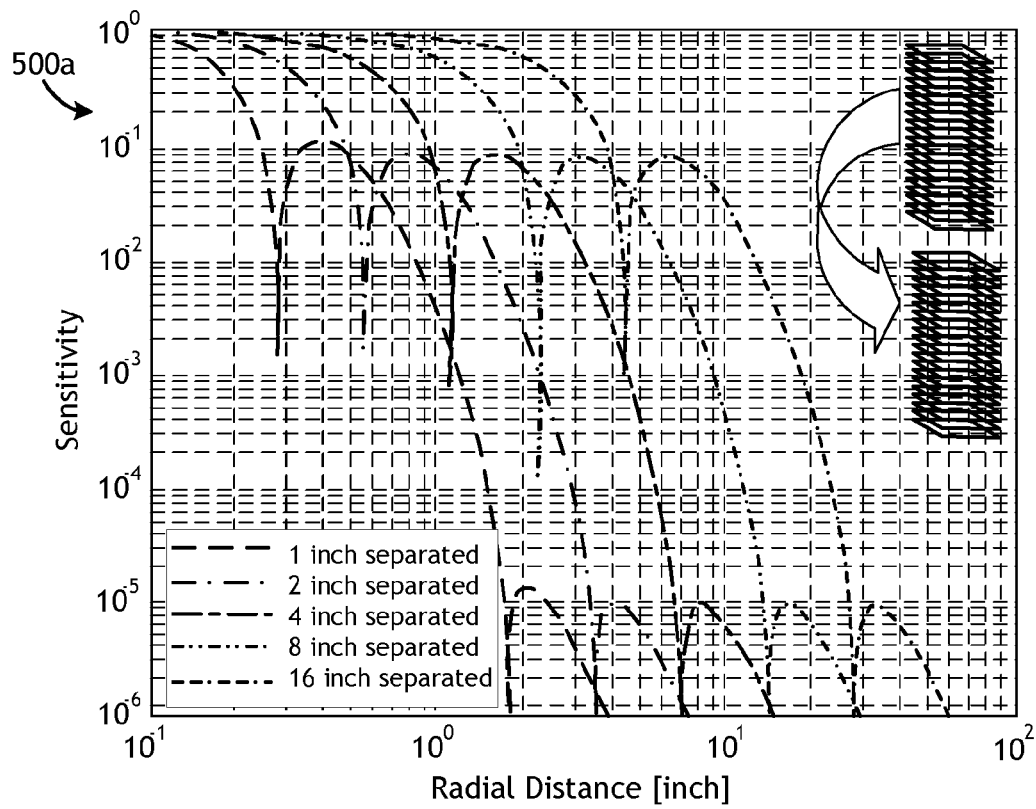
FIGS. 5A and 5B are plots showing the sensitivity of single separate transmitter and receiver antenna systems as a function of radial distance.
Figure 5B:
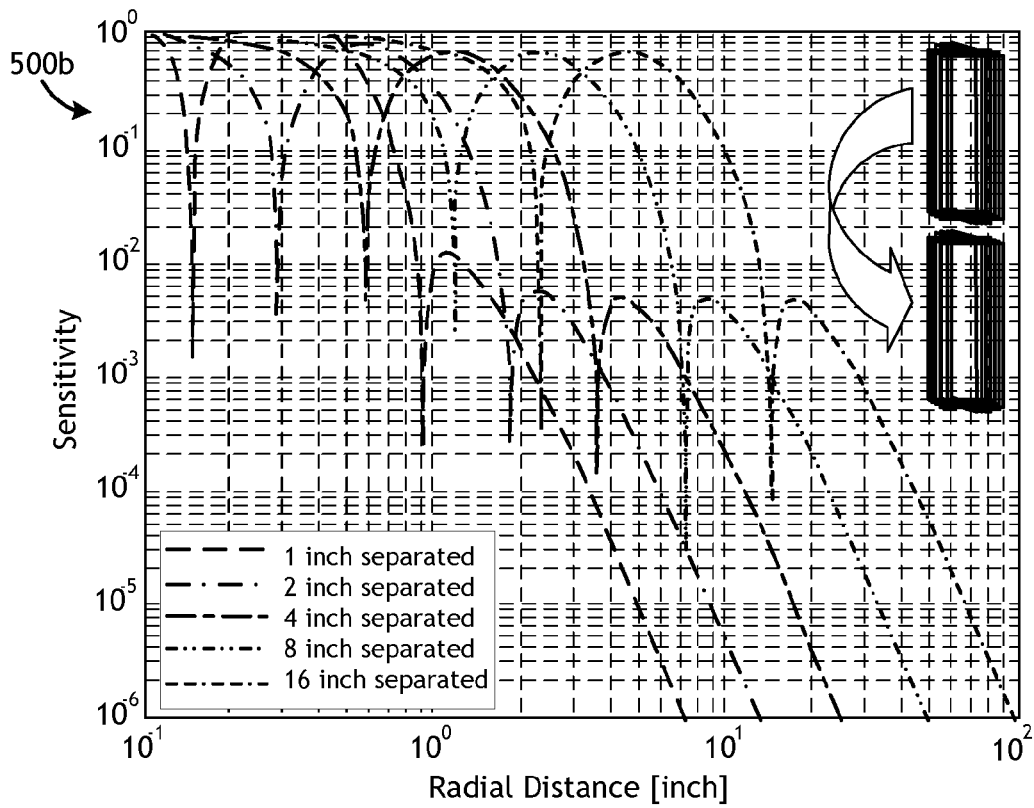

FIGS. 5A and 5B provide a first plot 500a and a second plot 500b, respectively, each showing the sensitivity of a single separate transmitter and receiver antenna system as a function of radial distance based on Born approximation in air environment with no pipe. More particularly, the first plot 500a shows axially-spaced transmitter and receiver antennas, where each transmitter and receiver antenna comprises only a z-coil (e.g., the z-coil 302 of FIGS. 3 and 4A-4B). The second plot 500b shows axially-spaced transmitter and receiver antennas, where each transmitter and receiver antenna comprises only x- and y-coils (e.g., the x- and y-coils 208, 210 of FIGS. 2, 3, and 4A-4B), with the y-coil orientation rotated by 90 degrees with respect to the x-coil orientation.

According to the Born approximation, an incident field is taken in place of a total field as the driving field at each point in a scattering plot, and a linear superposition method is applied to scattering by an extended body. Born approximation can be accurate if the scattered field is small in the scatterer, as compared to the incident field. Normally one would solve Maxwell's equations in three-dimensions to obtain accurate measurement data, but the Born approximation can be sufficiently accurate by approximating Maxwell's equations for scatters that are small (i.e., low scattering).

The first plot 500a graphically depicts the sensitivity with the z-coil, and the second plot 500b graphically depicts the sensitivity with the x- and y-coils, where the x and y-coils are identical but rotated by 90 degrees from each other. The depth (z) for sensitivity calculation is chosen as the measurement center, which is the mid-point between the transmitter and the receiver. The frequency is chosen as 10 Hz, and the sensitivity is calculated in the x-direction in each case where the z-coil or the x-coil are excited. The resulting curves shown in each plot 500a,b indicate different transmitter and receiver separation distances. As can be seen in FIGS. 5A and 5B, both z-coil and x- and y-coil systems can achieve high sensitivity at large radial distances when the separation between the transmitter and the receiver is selected to be large enough and they can focus deep into the environment they are in.

Figure 6A:
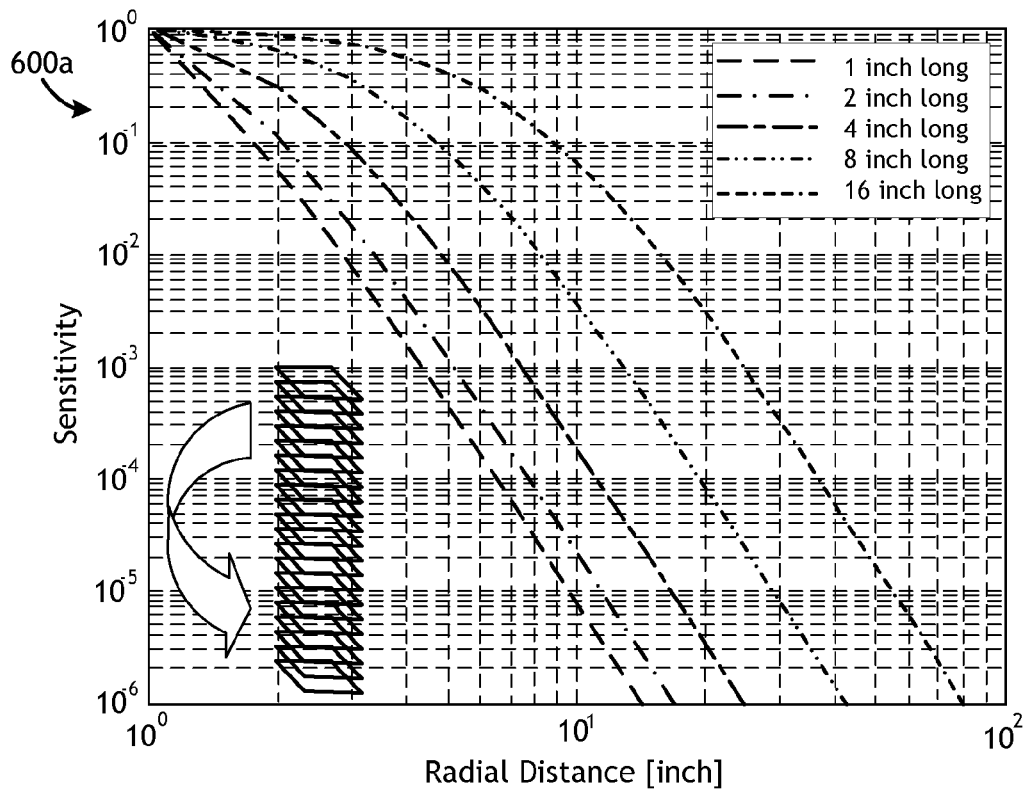
FIGS. 6A and 6B show the sensitivity of a single separate transmitter receiver system (i.e., transceiver) as a function of radial distance based on Born approximation in air environment with no pipe.
Figure 6B:
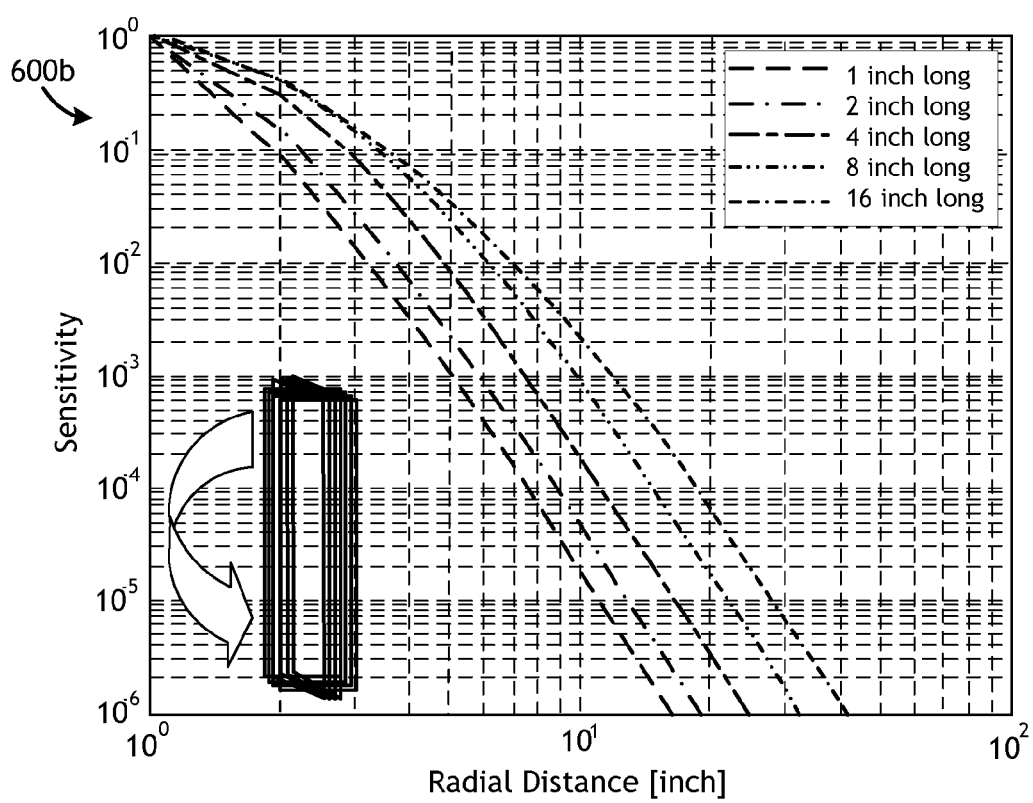

FIGS. 6A and 6B provide a first plot 600a and a second plot 600b, respectively, each showing the sensitivity of a single separate transmitter receiver system (i.e., transceiver) as a function of radial distance based on Born approximation in air environment with no pipe. The first plot 600a shows an elongated z-coil transceiver (e.g., the z-coil 302 of FIG. 4A) and the second plot 600b shows an elongated x- and y-coil (e.g., the x- and y-coils 208, 210 of FIGS. 2, 3, and 4A-4B) transceiver, with the y-coil orientation rotated by 90 degrees with respect to the x-coil orientation.

The short side of the rectangular-shaped transceivers is chosen to be 2 inches long. The depth (z) for sensitivity calculation is chosen as the measurement center, which is the mid-point of each transceiver. The resulting curves shown in the plots 600a,b represent different transceiver lengths. As can be seen in FIG. 6A, the z-coil transceiver can achieve a large depth of investigation, and the depth of investigation grows with increased transceiver length. On the other hand, the x- and y-coil transceiver of FIG. 6B shows diminishing returns as transceiver length is increased, and it only provides limited improvement. Accordingly, and in view of the plots 500a,b of FIGS. 5A and 5B, respectively, it can be seen that separated transmitter and receiver configurations may be more effective for sensing deep azimuthal pipe features.

Figure 7A:
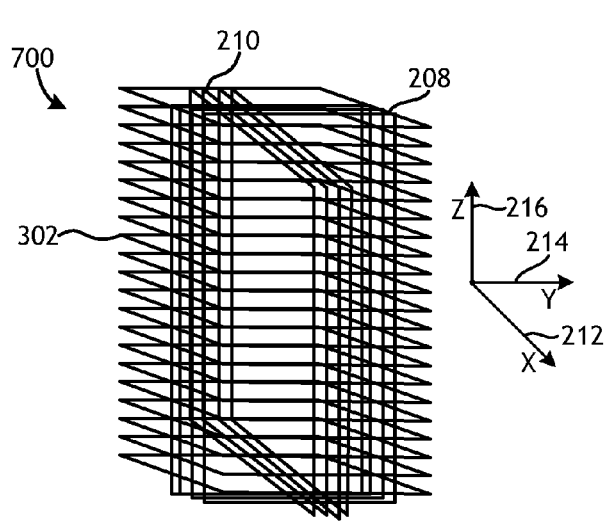
FIG. 7A depicts a three-axis antenna where the x- and y- and z-coils are collocated.

FIG. 7A depicts a three-axis antenna 700, according to one or more embodiments. The antenna 700 may be the same as or similar to the transmitter and receiver antennas 206a,b of FIG. 3 or the transceiver antenna 400 of FIG. 4A. More particularly, the antenna 700 may include the x-, y-, and z-coils 208, 210, 302 wrapped about a core (not expressly shown) to generate magnetic fields in mutually orthogonal directions. As indicated above, the x-coil 208 produces magnetic fields of a spatially distributed X magnetic dipole, the y-coil 210 produces magnetic fields of a spatially distributed Y magnetic dipole, and the z-coil 302 produces magnetic fields 218 of a spatially distributed Z magnetic dipole.

As depicted in FIG. 7A, the x-, y-, and z-coils 208, 210, 302 are collocated. This type of embodiment may prove advantageous since all the coils 208, 210, 302 will produce information about the same area of the pipe (e.g., the pipes 108a,b of FIGS. 2 and 3), which can provide more information about that zone as compared to a single coil. However, there may also be disadvantages of such a configuration. For instance, due to all the coils 208, 210, 302 using the same tool volume, less volume is available per coil 208, 210, 302, which may translate to less number of turns (i.e., windings) or less core material. Usually pipe inspection tools are expected to be very small in diameter since there is a considerably large number of small wellbore pipes that need to be inspected. As a result, the space in the pipe inspection tool can be very limited, especially when the placement of electrical boards and mechanical hardware (such as for pressure compensation and packaging) is also considered in addition to the coils 208, 210, 302 themselves.

Figure 7B:
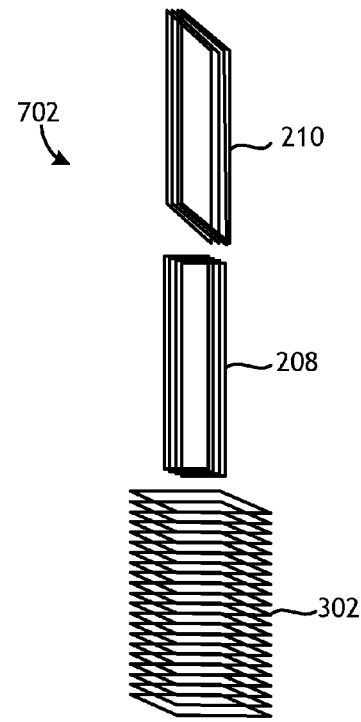
FIG. 7B depicts another three-axis antenna where the x- and y- and z-coils are staggered axially.

FIG. 7B depicts another three-axis antenna 702 where the x-, y-, and z-coils 208, 210, 302 are staggered axially, according to one or more embodiments. This type of configuration can be advantageous in terms of efficient use of space in a given pipe inspection tool, since each coil 208, 210, 302 occupies its own space in the pipe inspection tool. However, this configuration results in a longer pipe inspection tool, which may not be preferable from an operations point of view, and it also necessitates depth shifting of received data for joint interpretation of a selected pipe section. Depth shifting may not be desirable since it may result in additional errors and may complicate the overall system.

Figure 8A:
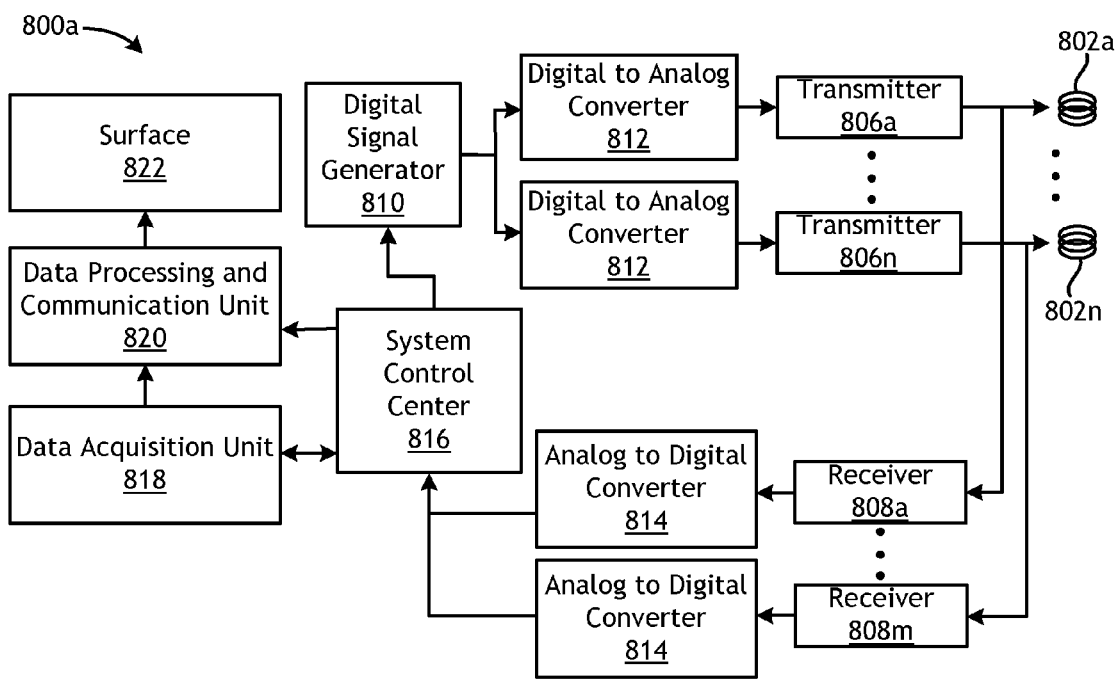
FIGS. 8A and 8B are block diagrams of exemplary data acquisition and control systems that may be used for monitoring pipes in a wellbore.
Figure 8B:
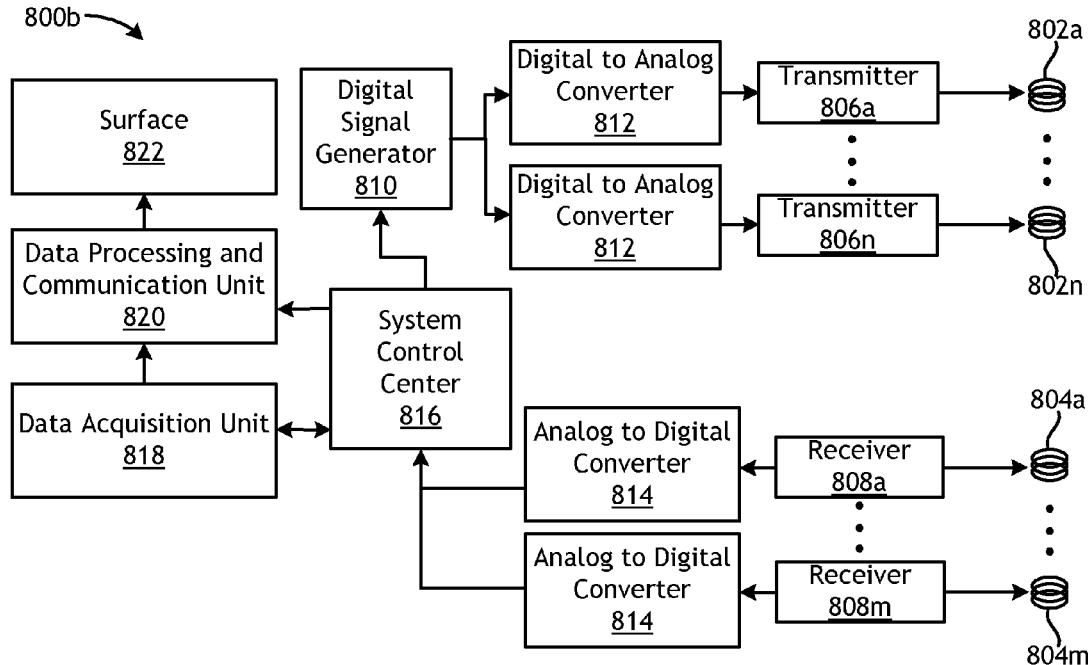

FIGS. 8A and 8B are block diagrams of exemplary data acquisition and control systems 800a and 800b, respectively, which may be used for monitoring pipes in a wellbore, according to one or more embodiments of the present disclosure. More particularly, the data acquisition and control system 800a of FIG. 8A may be used with transceiver antennas, such as the transceiver antenna 400 of FIG. 4A, and the data acquisition and control system 800b of FIG. 8B may be used with separated transmitter and receiver antennas, such as the transmitter and receiver antennas 206a,b of FIGS. 2, 3, and 4B. Those skilled in the art will readily appreciate that the data acquisition and control systems 800a,b described herein are merely examples of a wide variety of data acquisition systems that can operate in accordance with the principles of this disclosure. Accordingly, the data acquisition and control systems 800a,b are not to be limited solely to the specific details described herein and other changes or alterations to the structure and processing capabilities may be introduced without departing from the scope of the disclosure.

As illustrated, the data acquisition and control systems 800a,b may each include at least one transmitter antenna $802_a$-$802_n$. The data acquisition and control system 800b may further include at least one receiver antenna $804_a$-$804_m$, but in the data acquisition and control system 800a, the transmitter antennas $802_{a-n}$ may also operate as receiver antennas. Accordingly, the transmitter antennas $802_{a-n}$ of FIG. 8A may alternatively be characterized as transceivers. Each transmitting antenna $802_{a-n}$ in both data acquisition and control systems 800a,b may be driven by a corresponding transmitter $806_a$-$806_n$.

In FIG. 8A, the transmitter antennas $802_{a-m}$ (i.e., transceivers) may each be coupled to a dedicated receiver $808_{a-m}$ or a single receiver 808, and in FIG. 8B, each receiver antenna $804_{a-m}$ may be coupled to a corresponding receiver $808_{a-m}$. It should be noted that the number "m" of receiver antennas $804_{a-m}$ may be the same as, or different from, the number "n" of transmitter antennas $802_{a-n}$. It is also not necessary for the number of receiver antennas $804_{a-m}$ to be the same as the number of receivers $808_{a-m}$, or for the number of transmitter antennas $802_{a-n}$ to be the same as the number of transmitters $806_{a-n}$. Rather, any number of these elements or components may be used or otherwise employed without departing from the scope of the disclosure.

The data acquisition and control systems 800a,b may further include transmitter electronics that may include, for example, one or more of a signal generator 810, a digital-to-analog converter 812, a demultiplexer (not shown), and other modules or devices used to support operation of the transmitters $806_{a-n}$. The signal generator 810 may be configured to generate digital signals for transmission by the transmitters $806_{a-n}$, the digital-to-analog converters 812 may be configured to convert the digital signals to analog signals, and the demultiplexer may be configured to selectively couple the signal generator 810 to the transmitters $806_{a-n}$. As will be appreciated, any combination of one or more signal generators 810, digital-to-analog converters 812, and demultiplexers may be used to drive the transmitters $806_{a-n}$. Alternatively, the transmitters $806_{a-n}$ may each perform the function of the signal generator 810, and the signal generator 810 may otherwise be omitted from the data acquisition and control systems 800a,b.

The receivers $808_{a-m}$ may be coupled to receiver electronics, which may include, for example, one or more analog-to-digital converters 814 and other modules or devices used to support operation of the receivers $808_{a-m}$. A system control center 816 may communicably couple the transmitter and receiver electronics and thereby control overall operation of the data acquisition and control systems 800a,b. The system control center 816 may further be communicably coupled to at least a data acquisition unit 818 and a data processing and communication unit 820, thereby placing the receiver electronics also in communication with such components. In some embodiments, the data acquisition unit 818 may be configured to determine an amplitude and/or a phase of a received signal. The acquired signal information may be stored, along with acquisition time information in a data buffer of the data acquisition unit 818.

The data buffer may be useful when pipe characteristics or features are determined based on signals received at different times and/or at different positions within a wellbore.

Data processing may be performed at the earth's surface or at a downhole location where the data acquisition and control systems 800a,b are arranged. If the data processing is to be performed at the surface, the acquired signal information from the receiver electronics, the data acquisition unit 818, and the buffered signal information from the data buffer may be conveyed to the data processing and communication unit 820, which may be configured to transmit the data to the surface 822 and to a computer or other processing system (not shown) arranged at the surface 822. For instance, the data may be transmitted to the logging facility 120 and associated computing facilities 122 of FIG. 1. If the data processing is to be performed downhole, however, the data processing and communication unit 820, in conjunction with the other components of the data acquisition and control systems 800a,b, may be configured to perform the necessary data processing.

Both the computer at the surface 822 (e.g., the computing facilities 122 of FIG. 1) and the system control center 816 may include multiple processors and a memory configured to receive and store data. The memory may be any non-transitory machine-readable medium that has stored therein at least one computer program with executable instructions that cause the processor(s) to perform the data processing on the received signals. The memory may be, for example, random access memory (RAM), flash memory, read only memory (ROM), programmable read only memory (PROM), electrically erasable programmable read only memory (EEPROM), registers, hard disks, removable disks, a CD-ROM, a DVD, any combination thereof, or any other suitable storage device or medium.

Since the system control center 816 is coupled to various components of the data acquisition and control systems 800a,b, the system control center 816 may be configured to adjust or otherwise regulate various parameters of the data acquisition and control systems 800a,b in order to optimize operation. For example, the system control center 816 may control the frequencies generated by the signal generator 810 in the transmitter electronics or the transmitters $806_{a-n}$. The system control center 816 may also control the timing of the transmitters $806_{a-n}$. For instance, the system control center 816 may cause the transmitters $806_{a-n}$ to operate such that a time-varying signal is generated at the transmitter antennas $802_{a-n}$. The time-varying signal may be sinusoidal with the phase and amplitude of it controlled to a desired value. It may also be a pulse of different shape such as rectangular or triangular.

The digital-to-analog converters 812 may be used to generate electrical signals on the transmitters $806_{a-n}$ that are stored or defined in digital form. The signals that are generated at the transmitters $806_{a-n}$ are coupled electromagnetically to the features or characteristics of the wellbore pipes that are next to the transmitter antennas $802_{a-n}$ and generate eddy currents, which generate secondary currents. These secondary currents contain information about the characteristics of the pipes and they are received by the transmitter antennas $802_{a-n}$ acting as transceivers in FIG. 8A, or by the receiver antennas $804_{a-m}$ of FIG. 8B.

In the case of frequency-domain operation, the received signals can be represented as voltage or current numbers in complex domain with real and imaginary parts, in phasor domain as amplitude and phase, or any other domain that can be obtained by analytical mapping from any of these domains. In the time-domain operation, received signals are magnitudes as a function of time, which can be positive or negative. Results from time and frequency domain can be transferred from one to another by using Fourier transform or inverse Fourier transform. Results may be transferred from analog to digital domain through the use of the analog-to-digital converters 814.

In addition to the eddy currents, which exhibit pipe feature (characteristic) information, a direct coupling from the transmitters $806_{a-n}$ to the receivers $808_{a-m}$ exists. In the case of separated transmitters $806_{a-n}$ and receivers $808_{a-m}$, this coupling term is relatively small, however, it can get relatively big in the case of collocated transmitters $806_{a-n}$ and receivers $808_{a-m}$. This direct coupling can be removed by software through the use of an additive term, which is computed in an air calibration step. An alternative is to remove the coupling by cancelling it out with signal from a secondary transmitter $806_{a-n}$.

In other embodiments, a pulsed excitation may be used with temporally separated transmitting and receiving cycles. In the listening period, the direct coupling dies out polynomially or exponentially and only reflections, scattering, or eddy currents from the features are received. In the sinusoidal type excitation, the length of the listening period determines the signal-to-noise ratio (SNR) of the system. Longer listening times are required to improve SNR, while this also causes slower logging speeds for a fixed vertical resolution for the system.

The sampling frequency also can be optimized to reduce noise while producing enough definition in time to resolve pipe features at different distances to the pipe inspection tool. Listening time is also an important parameter, since features of the pipes that are far away generally arrive at late time. Since downhole memory is limited, it is important to minimize listening time while still maintaining the sensitivity to features that are further away from the pipe inspection tool, such as features (characteristics) of second or third pipes. For a specific transmitter $806_{a-n}$ excitation, multiple receivers $808_{a-m}$ can be recorded at the same time. Similarly, multiple transmitters $806_{a-n}$ can be operated at the same time and they can be time, frequency, or jointly multiplexed for later demultiplexing operations at the receivers $808_{a-m}$. Upon reception of the signals, they are digitized, stored in a buffer, preprocessed, and sent to the surface 822 using the data processing and communication unit 820. The data may later be inverted and the results of the inversion or raw data can be visualized. Decisions on what to do with the pipes being monitored can be made based on the visualization logging or production.

The main difference between the data acquisition and control systems 800a,b (i.e., transceiver and separate transmitter-receiver configurations, respectively) is in the dynamic range of the system and type of electronic design that will be used. A transceiver-type system, for example, requires good control on the transmitting pulse since any ringing in the electronics can impede reception of much smaller received response signals. However, since the same transmitter antenna $802_{a-n}$ (i.e., transceiver) is used for transmitting and receiving in the first data acquisition and control system 800a, significant savings in space can be made, which can translate to space for more windings or higher quality electronics or mechanical parts (such as pressure compensation).

Figure 9:
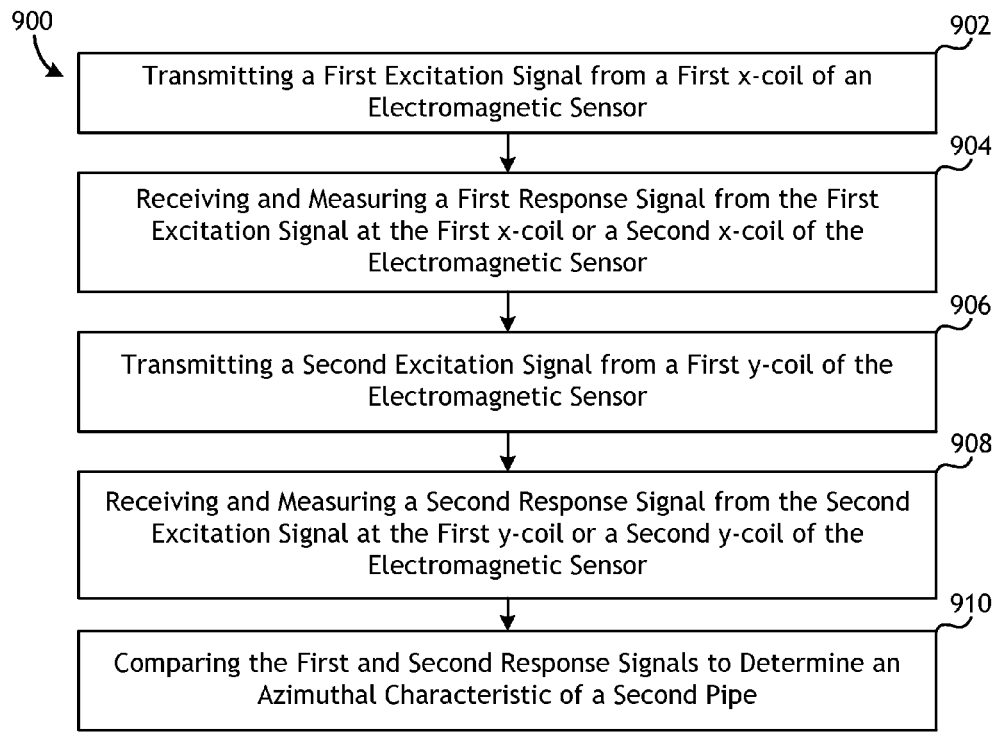
FIG. 9 is a schematic flowchart of a first exemplary interpretation method.

FIG. 9 is a schematic flowchart of a first interpretation method 900, according to one or more embodiments. The method 900 may be undertaken using any of the pipe inspection tools described herein within a wellbore having at least a first pipe and a second pipe (i.e., the first and second pipes 108a,b of FIGS. 2 and 3) positioned therein. According to the method 900, a first excitation signal is transmitted from a first x-coil of an electromagnetic sensor, as at 902. A first response signal derived from the first excitation signal is then received and measured at the first x-coil or a second x-coil of the electromagnetic sensor, as at 904. A second excitation signal may then be transmitted from a first y-coil of the electromagnetic sensor, as at 906, and a second response signal from the second excitation signal is then received and measured at the first y-coil or a second y-coil of the electromagnetic sensor, as at 908.

The first and second excitation signals may be transmitted at the same frequency and otherwise considered the same type or magnitude of excitation signal. The length of the first and second x- and y-coils and the frequency and time of the first and second excitation signals may be adjusted in such a way that sensitivity to wellbore pipes beyond the first or innermost pipe is maximized. The first and second response signals received at the first or second x-coils and the first or second y-coils, respectively, may be recorded for each of the first x- and y-coil transmissions.

The first and second response signals may then be compared to determine an azimuthal characteristic on a second pipe, as at 910. Example azimuthal characteristics that may be determined include, but are not limited to, the presence of a defect (e.g., corrosion, fractures, holes, and decreased wall thickness or variation in the physical, chemical, or electrical properties of the material, such as electrical conductivity or magnetic permeability) in the pipes. If the first response signal is sufficiently larger than the second response signal, this may be an indication of an azimuthal characteristic on any pipe beyond first pipe or eccentricity of the pipe inspection tool.

This determination could be communicated to a well operator as a binary curve, i.e., the difference being larger than a threshold or not as a function of depth. Threshold here can be set to a value, which is larger than measurement errors due to electronics noise. The difference in the first and second response signals received at the first or second x-coils and the first or second y-coils, respectively, can also be communicated in percentage, i.e., (Sx−Sy)/Sx, (SxSy)/Sy or (Sx−Sy)/max(Sx,Sy), where "max" is the maximum of the two arguments provided. This method can be used in conjunction with first pipe inspection methods to assist making the distinction between signals due to first pipe features and features of any pipe radially beyond the first pipe.

Figure 10:
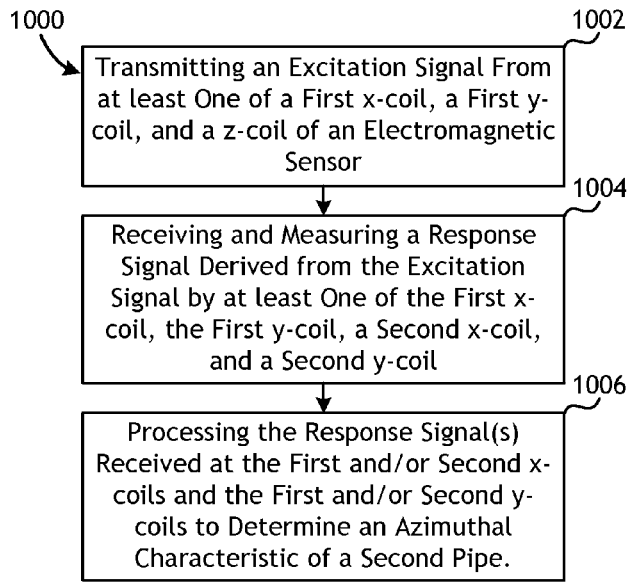
FIG. 10 depicts a schematic flowchart of a second exemplary interpretation method.

FIG. 10 is a schematic flowchart of a second interpretation method 1000, according to one or more embodiments. Similar to the method 900 of FIG. 9, the method 1000 may be undertaken using any of the pipe inspection tools described herein within a wellbore having at least a first pipe and a second pipe (i.e., the first and second pipes 108a,b of FIGS. 2 and 3) positioned therein. According to the method 1000, an excitation signal is transmitted from at least one of a first x-coil, a first y-coil, and a z-coil of an electromagnetic sensor, as at 1002. In the event more than one excitation signal is transmitted, the excitation signals may be transmitted at the same frequency and otherwise considered the same type or magnitude of signal. The length of the first x-, first y-, and z-coils and the frequency and time of the excitation signal(s) may be adjusted in such a way that sensitivity to wellbore pipes beyond the first or innermost pipe is maximized.

A response signal derived from the excitation signal is then received and measured by at least one of the first x-coil, the first y-coil, a second x-coil of the electromagnetic sensor, and a second y-coil of the electromagnetic sensor, as at 1004. The response signal(s) received at the first and/or second x-coils and the first and/or second y-coils may be recorded for each of the x-, y-, and z-coil transmissions. The response signal(s) is then processed to determine an azimuthal characteristic on the second pipe, as at 1006. In some embodiments, processing the response signals, as at 1006, may include comparing the response signals to modeled signals from a computer model. The computer model may be created as a function of various characteristics associated with pipes beyond the first pipe. A numerical optimization problem may then be solved to minimize a difference between the response signals and the modeled signals by conducting a search in the pipe characteristic space. The pipe characteristic that produces the smallest difference between the modeled signal and response signal may be taken as the solution.

Figure 11:
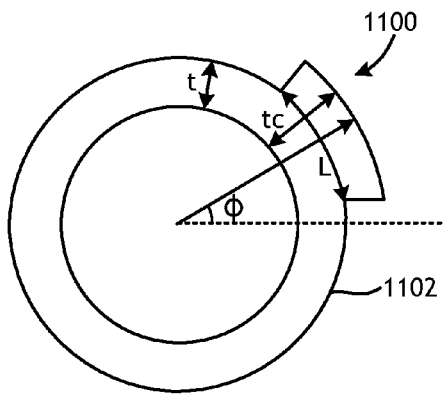
FIG. 11 depicts a parametric pipe model with a small number of assumed unknowns.

Due to small number of diverse measurements, it is not possible to solve for a very detailed set of pipe characteristics or features. As a result, a parametric pipe model with a small number of unknowns needs to be assumed, such as that shown in FIG. 11. In this case, a model 1100 of an exemplary pipe 1102 is depicted. The pipe 1102 may be similar to or the same as the pipes 108a,b of FIGS. 2 and 3. The pipe 1102 may exhibit various parameters, such as a pipe thickness with corrosion (tc), a pipe thickness without corrosion (t), a pipe conductivity (σ), a pipe magnetic permeability (μ), a pipe corrosion azimuth (φ) and a pipe corrosion arcuate length (L). The pipe corrosion arcuate length (L) may be used where corrosion is assumed to be uniform over the length (L) of the corroded section.

It should be noted that due to symmetry of the x- and y-coil designs, there will always be an ambiguity of 180° in the inversion results. Such ambiguity, however, may be resolved by using complementary inspection methods that are azimuthal, such as eddy current imaging on sensor pads, or by incorporating a priori knowledge about the occurrence mechanism of corrosion (in relation to gravity, etc.). Similar to the first interpretation method 900 of FIG. 9, the second interpretation method 1000 of FIG. 10 can be used in conjunction with first pipe inspection methods to assist making the distinction between signals due to first pipe features (characteristics), and features of any pipe radially beyond the first pipe.

Figure 12:
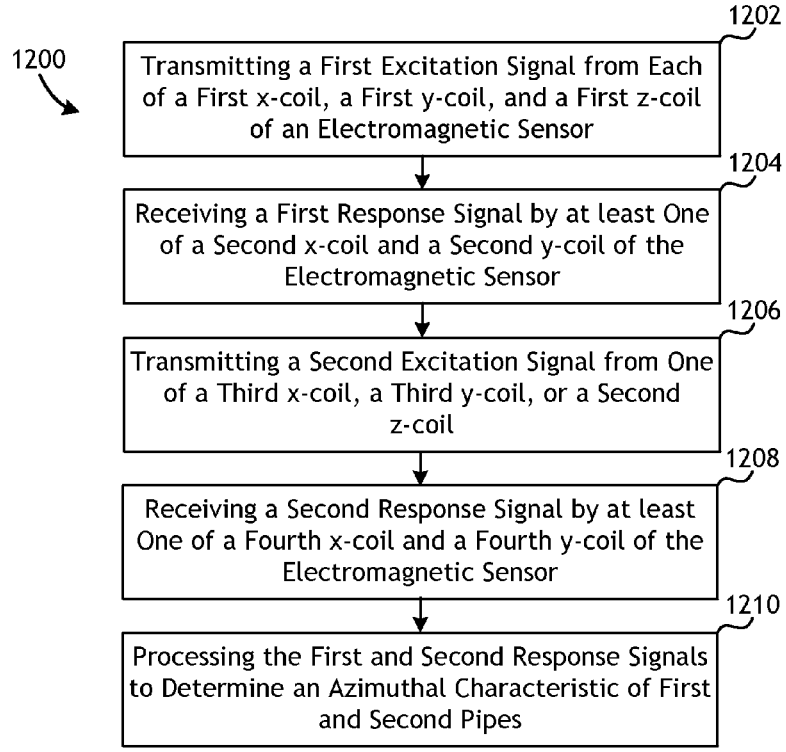
FIG. 12 depicts a schematic flowchart of a third exemplary interpretation method.
Figure 12A:
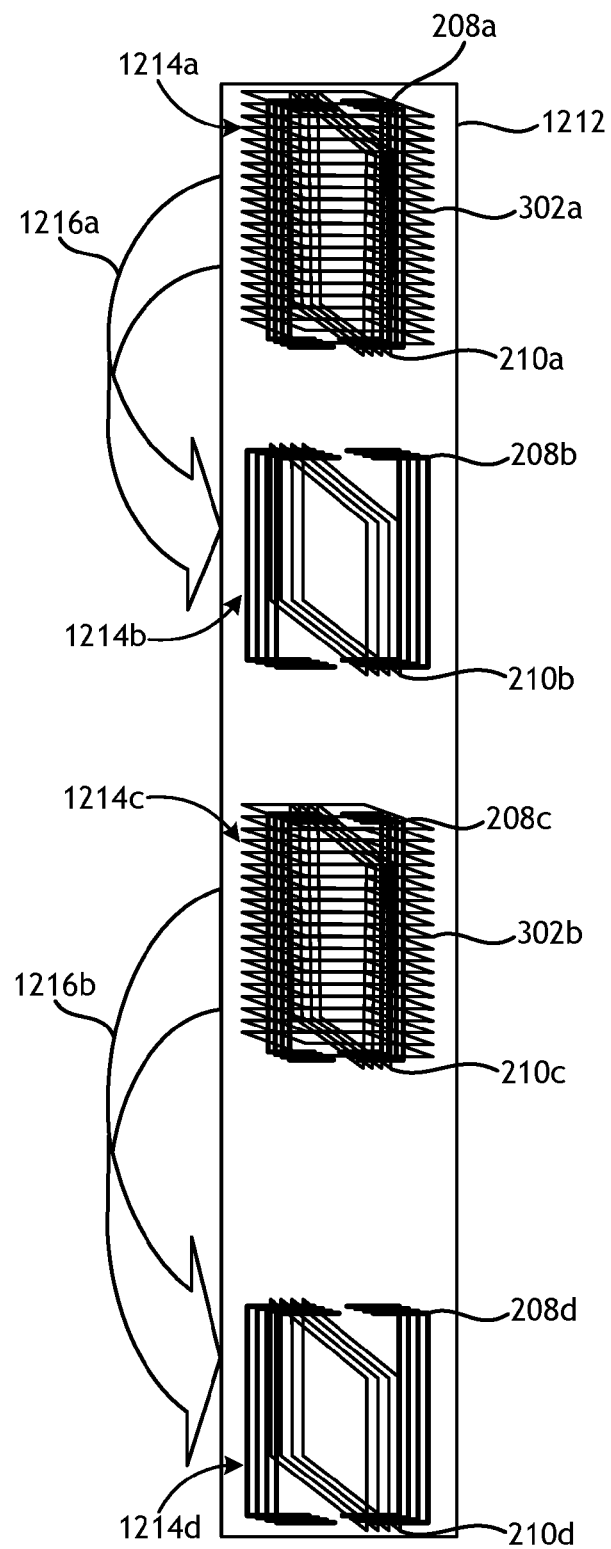
FIG. 12A is a schematic diagram of an example pipe inspection tool used to carry out the method of FIG. 12.

FIG. 12 is a schematic flowchart of a third interpretation method 1200, according to one or more embodiments, and FIG. 12A is a schematic diagram of an example pipe inspection tool 1212 that may be used to carry out the method 1200. The method 1200 may be undertaken using the pipe inspection tool 1212 within a wellbore having at least a first pipe and a second pipe (i.e., the first and second pipes 108a,b of FIGS. 2 and 3) positioned therein. According to the method 1200, a first excitation signal is transmitted from each of a first x-coil, a first y-coil, and a z-coil of an electromagnetic sensor, as at 1202. A first response signal derived from the first excitation signal is then received and measured by at least one of a second x-coil and a second y-coil of the electromagnetic sensor, as at 1204. A second excitation signal may then be transmitted from one of a third x-coil, a third y-coil, or a second z-coil, as at 1206. A second response signal derived from the second excitation signal may then be received and measured by at least one of a fourth x-coil and a fourth y-coil of the electromagnetic sensor, as at 1208. Finally, the first and second response signals may be processed to determine an azimuthal characteristic of the first and second pipes, as at 1210.

With reference to FIG. 12A, the first antenna 1214a includes the first x-coil 208a, the first y-coil 210a, and a first z-coil 302a and produces the first excitation signal 1216a. The second antenna 1214b includes the second x-coil 208b and the second y-coil 210b, and receives and measures the response signal derived from the first excitation signal 1216a. The third antenna 1214c includes the third x-coil 208c, the third y-coil 210c, and the second z-coil 302b and produces the second excitation signal 1216b. The fourth antenna 1214d includes the fourth x-coil 208d and the fourth y-coil 210d, and receives and measures the response signal derived from the second excitation signal 1216b. The axial separation distance between the first and second antennas 1214a, 1214b may be adjusted and the first excitation signal 1216a frequency or listening time may be set to have maximum sensitivity to first pipe features, and minimized sensitivity to any pipe radially beyond the first pipe. Similarly, the axial separation distance between the third and fourth antennas 1214c, 1214d may be adjusted, and the second excitation signal 1216b frequency or listening time may be set to have maximum sensitivity to features of pipes radially beyond the first pipe, and minimized sensitivity to the first pipe. This results in sensitivity of the second signal measurement being deeper than the first pipe. In at least one embodiment, the axial separation distance between the third and fourth antennas 1214c, 1214d is greater than the axial separation distance between the first and second antennas 1214a, 1214b.

Again, due to the small number of diverse measurements, it may not be possible to solve for a very detailed set of pipe features (i.e., azimuthal characteristics). As a result, a parametric pipe model with a small number of unknowns may be assumed, such as that shown in FIG. 11, but for each pipe separately. In this case, a model with a first pipe thickness with pipe corrosion (tc), first pipe thickness without corrosion (t), first pipe conductivity ($\sigma$), first pipe magnetic permeability ($\mu$), first pipe corrosion azimuth ($\phi$), first pipe corrosion length (L), second pipe thickness with pipe corrosion (tc), second pipe thickness without corrosion (t), second pipe conductivity ($\sigma$), second pipe magnetic permeability ($\mu$), second pipe corrosion azimuth ($\phi$), second pipe corrosion length (L) can be used where corrosion is assumed to be uniform over the length of the corroded section in both first and second pipes. One or more of the parameters that are listed above may be known a priori and may not need to be inverted, which simplifies the inversion process. In addition, the above method may be applied for inversion of features of three or more pipes. For example, in case the first pipe features are already known (through a separate complementary pipe inspection tool or a priori knowledge) the same inversion could be performed on second and third pipes in the place of first and second.

Figure 13:
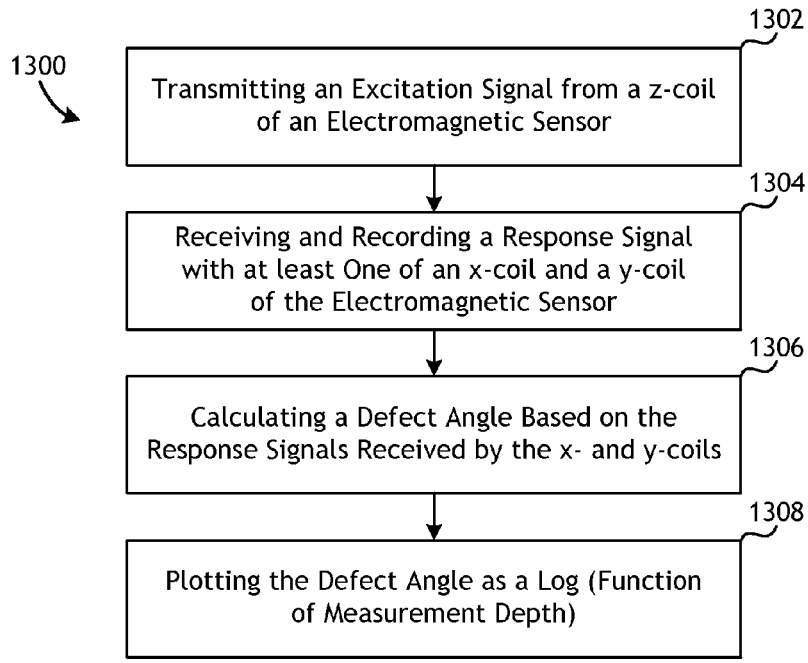
FIG. 13 depicts a schematic flowchart of a fourth exemplary interpretation method.

FIG. 13 is a schematic flowchart of a fourth interpretation method 1300, according to one or more embodiments. Similar to the methods 900, 1000, and 1200 of FIGS. 9, 10, and 12, respectively, the method 1300 may be undertaken using any of the pipe inspection tools described herein within a wellbore having at least a first pipe and a second pipe (i.e., the first and second pipes 108a,b of FIGS. 2 and 3) positioned therein. According to the method 1300, an excitation signal is transmitted from a z-coil of an electromagnetic sensor, as at 1302. A response signal derived from the excitation signal may then be received and recorded by at least one of an x-coil and a y-coil of the electromagnetic sensor, as at 1304. In some embodiments, the x-, y-, and z-coils are collocated in a single transceiver antenna, similar to the three-axis antenna 700 of FIG. 7A. In other embodiments, however, the x-, y-, and z-coils may be staggered, similar to the three-axis antenna 702 of FIG. 7B.

A defect angle may then be calculated based on the response signals received by the x- and y-coils, as at 1306. The defect angle may be calculated by using the formula $\phi=\text{angle}(S_{zx}, S_{zy})$, where $S_{zx}$ is the response signal received at the x-coil due to the z-coil excitation signal, $S_{zy}$ is the response signal received at the y-coil due to the z-coil excitation signal, and angle is the angle of the vector with respect to the x-axis with x- and y-coordinates as given by the first and second arguments respectively. It should be noted that signals $S_{zx}$ and $S_{zy}$ are chosen as the scalar signals at the same frequency or time, or any analytical function or combination of both. For example, the response signals may be the complex voltages that are received at 1 Hz each. As a second example, the response signals may be the real valued voltages that are received at 1 ms each. Finally, the defect angle may be plotted as a log (function of measurement depth), as at 1308. The defect angle may be indicative of angle or orientation of pipe defects in the first and second pipes.

Figure 14:
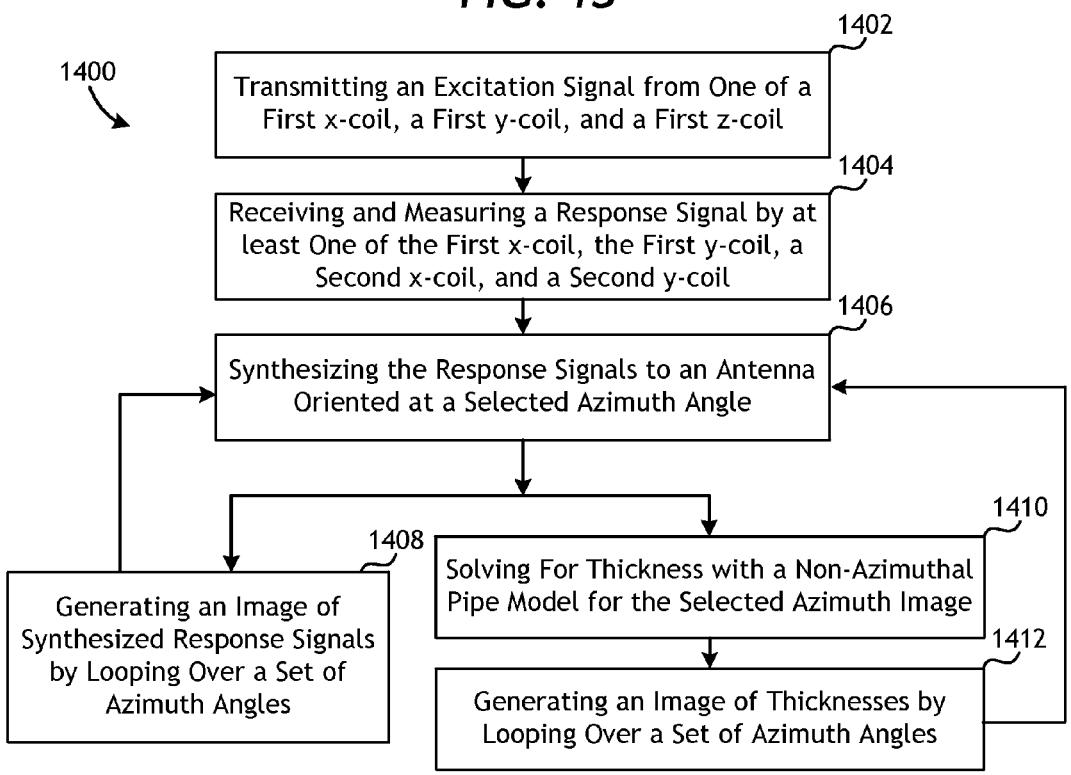
FIG. 14 depicts a schematic flowchart of a fifth exemplary interpretation method.

FIG. 14 is a schematic flowchart of a fifth interpretation method 1400, according to one or more embodiments. Similar to the methods 900, 1000, 1200, and 1300 of FIGS. 9, 10, 12, and 13, respectively, the method 1400 may be undertaken using any of the pipe inspection tools described herein within a wellbore having at least a first pipe and a second pipe (i.e., the first and second pipes 108a,b of FIGS. 2 and 3) positioned therein. According to the method 1400, an excitation signal may be transmitted from one of a first x-coil, a first y-coil, and a first z-coil of an electromagnetic sensor, as at 1402. A response signal derived from the excitation signal may then be received and measured by at least one of the first x-coil, the first y-coil, a second x-coil, and a second y-coil of the electromagnetic sensor, as at 1404.

Next, the response signals may be synthesized to an antenna oriented at a selected azimuth angle, as at 1406. To accomplish this, the response signals that correspond to different pipe inspection tool rotation angles are synthesized and calculated as a function of azimuth angle and depth within the wellbore. Lastly, an image of the synthesized response signals may be generated by looping over a set of azimuth angles, as at 1408. That is, after the thickness of every depth and every angle is generated, the results can be displayed as a two-dimensional image with the first dimension representing axial position along the wellbore and the second dimension representing the azimuth angle.

The calculation of the image based on the synthesized response signals, as at 1408, may be performed using the following Equations:

$$S(\phi_T,\phi_R)=(\hat{x}\cos(\phi_T)+\hat{y}\sin(\phi_T))*(\hat{x}\cos(\phi_R)+\hat{y}\sin(\phi_R))\cdot$$
$$(\hat{x}\hat{x}S_{xx}+\hat{x}\hat{y}S_{xy}+\hat{x}\hat{z}S_{xz}+\hat{y}\hat{x}S_{yx}+\hat{y}\hat{y}S_{yy}+\hat{x}\hat{y}S_{yz}+\hat{z}\hat{x}S_{zx}+$$
$$\hat{z}\hat{y}S_{zy}+\hat{z}\hat{z}S_{zz})=(\hat{x}\hat{x}\cos(\phi_T)\cos(\phi_R)+\hat{x}\hat{y}\cos(\phi_T)\sin$$
$$(\phi_R)+\hat{y}\hat{x}\sin(\phi_T)\cos(\phi_R)+\hat{y}\hat{y}\sin(\phi_T)\sin(\phi_R))\cdot$$
$$(\hat{x}\hat{x}S_{xx}+\hat{x}\hat{y}S_{xy}+\hat{x}\hat{z}S_{xz}+\hat{y}\hat{x}S_{yx}+\hat{y}\hat{y}S_{yy}+\hat{x}\hat{y}S_{yz}+\hat{z}\hat{x}S_{zx}+$$
$$\hat{z}\hat{y}S_{zy}+\hat{z}\hat{z}S_{zz})=(S_{xx}\cos(\phi_T)\cos(\phi_R)+S_{xy}\cos(\phi_T)\sin$$
$$(\phi_R)+S_{yx}\sin(\phi_T(\cos(\phi_R)+S_{yy}\sin(\phi_T)\sin(\phi_R))$$
$$S(\phi)=S_{xx}\cos^2(\phi)+(S_{xy}+S_{yx})\cos(\phi)\sin(\phi)+S_{yy}\sin^2(\phi)$$

Equation (1)

$$S(\phi)=\hat{z}*(\hat{x}\cos(\phi)+\hat{y}\sin(\phi))\cdot(\hat{x}\hat{x}S_{xx}+\hat{x}\hat{y}S_{xy}+\hat{x}\hat{z}S_{xz}+\hat{y}\hat{x}S_{yx}+$$
$$\hat{y}\hat{y}S_{yy}+\hat{x}\hat{y}S_{yz}+\hat{z}\hat{x}S_{zx}+\hat{z}\hat{y}S_{zy}+\hat{z}\hat{z}S_{zz})=(\hat{z}\hat{x}\cos(\phi)+\hat{z}\hat{y}$$
$$\sin(\phi))\cdot(\hat{x}\hat{x}S_{xx}+\hat{x}\hat{y}S_{xy}+\hat{x}\hat{z}S_{yz}+\hat{y}\hat{x}S_{yx}+\hat{y}\hat{y}S_{yy}+\hat{x}\hat{y}S_{yz}+$$
$$\hat{z}\hat{x}S_{zx}+\hat{z}\hat{y}S_{zy}+\hat{z}\hat{z}S_{zz})=S_{zx}\cos(\phi)+S_{zy}\sin(\phi)$$

Equation (2)

where $S_{ab}$ is the signal at b-receiver when a-transmitter is activated, where a is one of {x,y,z} and b is also one of {x,y,z}, $\phi$ is the azimuthal angle, $\phi_T$ is the azimuthal angle of the transmitter, $\phi_R$ is the azimuthal angle of the receiver, and sin and cos are trigonometric functions. Here, Equation (1) can be used to calculate the azimuthal image from X- and Y-measurements only, and Equation (2) can be used to create the image from Z-measurements.

In order to create an image, Equations (1) or (2) are executed at a number of azimuths ranging from 0° to 360°, and also at different depths within the wellbore, which produces a two-dimensional image. This image can then be presented on a log.

It is also possible to create a pseudo-image of pipe thicknesses from the images that are produced from Equations (1) and (2). This is accomplished by using one azimuth and depth result at a time to invert for pipe features and plotting the calculated pipe parameters as a function of azimuth and depth. As indicated in the method 1400, thickness may be solved with a non-azimuthal pipe model for the selected azimuth angle, as at 1410. An image of the thicknesses may then be generated by looping over a set of azimuth angles, as at 1412. That is, after the thickness for every depth and every angle is generated, the results can be displayed as a two-dimensional image with the first dimension representing axial position along the wellbore and the second dimension representing the azimuth angle.

Figure 15:
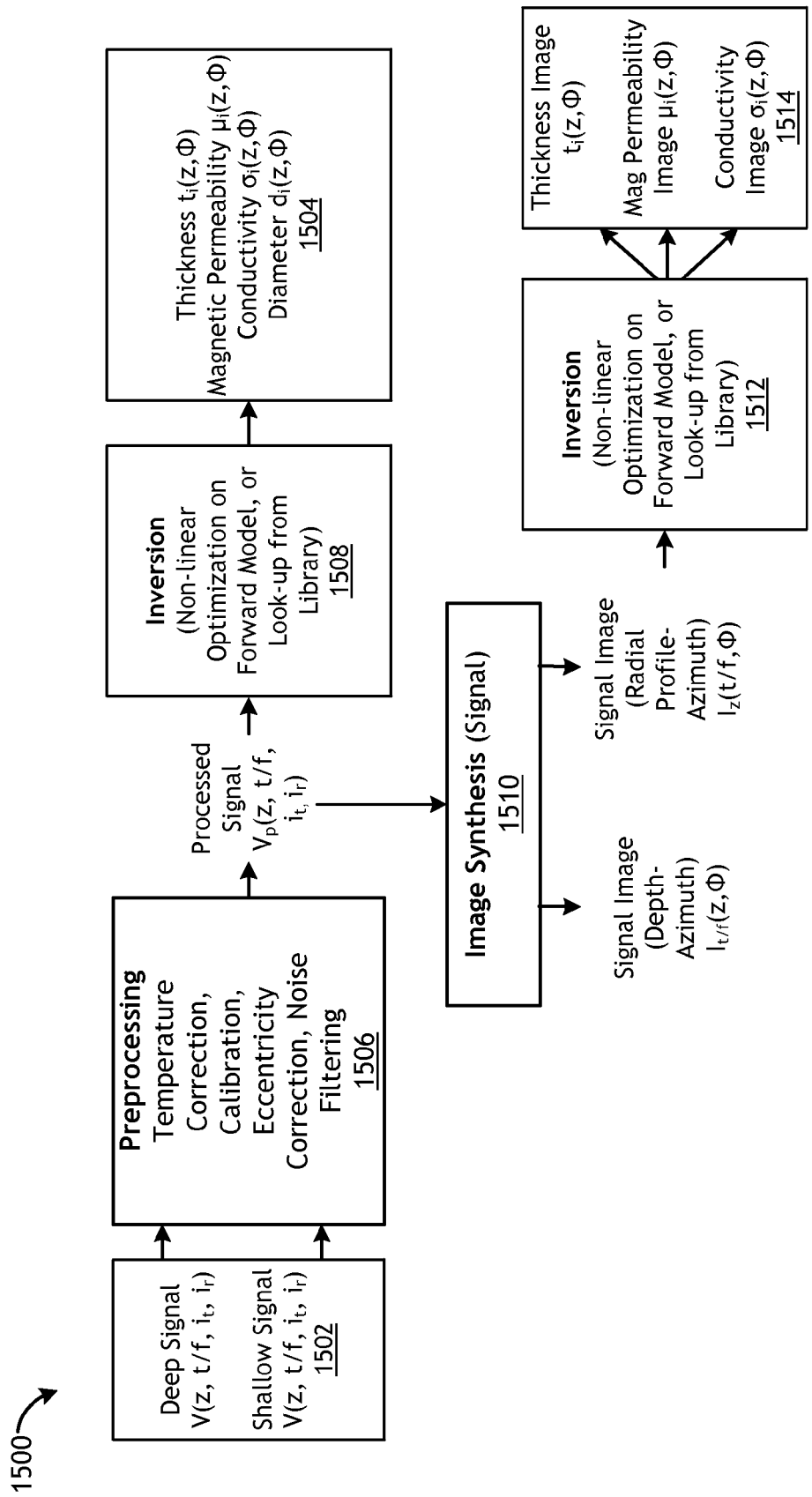
FIG. 15 depicts a schematic diagram of an exemplary inversion methodology.

FIG. 15 is a schematic flowchart of a method 1500 that shows a more detailed description of the presently described inversion methodology. More particularly, the method 1500 may take measurement data 1502 in the form of deep and shallow impedance signals V at depth z and convert them into one or more pipe characteristics 1504 such as, but not limited to, thickness, magnetic permeability, conductivity, and diameter measurements of any of the pipes.

In the illustrated method, deep and shallow signals V are measured at time t (for frequency and time-based systems) at antenna depth z between the antenna terminals $i_{r1}$ and $i_{r2}$ as a result of excitation between the antenna terminals $i_{t1}$ and $i_{t2}$. The received signals V and, more particularly, the transmitter index $i_t$ and the receiver index $i_r$, may then be preprocessed, as at 1506. Preprocessing the measurement data 1502 may include performing temperature corrections through the use of correlation tables or performing "software focusing" to remove drifts in the electronics. Preprocessing the measurement data 1502 may also include calibration, which may include normalization with the excitation signal amplitude, eccentricity (stand-off) correction, to remove the effect of a sensor pad (if used) not touching the pipe, and temporal or spatial filters to reduce noise.

The preprocessed signal Vp may then be fed to an inversion algorithm, as at 1508, which looks up the measured signal in a database that contains mappings between modeled signals and pipe features (thickness, magnetic permeability, conductivity and diameter). The pipe characteristics corresponding to the modeled signal that matches with least mismatch with the measured processed signal may then be selected. When applied at different depths, the inversion algorithm may yield various pipe characteristics 1504, such as thickness, magnetic permeability, conductivity and diameter of the pipe as a function of depth and azimuth in the wellbore.

The preprocessed signal Vp may optionally be synthesized to obtain signal image parameters, as at 1510. A similar inversion algorithm or method may be applied on the synthesized signal images at different depth, azimuth, time or frequency, as at 1512. The resulting signals may be plotted as a function of depth and azimuth, which yields traditional logging pipe images, as at 1514. Signals may also be plotted as a function of time/frequency and azimuth, which yields a cross-section view of the hole since different frequency and time is influenced by different pipes. Finally, thickness, magnetic permeability and conductivity from the inversion results may be plotted as a function of depth z and azimuth, as at 1514.

Embodiments disclosed herein include a method that includes conveying a pipe inspection tool into a wellbore having at least a first pipe positioned within a second pipe, the pipe inspection tool including an electromagnetic sensor, transmitting at least one excitation signal from one or more x-, y-, or z-coils of the electromagnetic sensor, receiving and measuring a first response signal derived from the first excitation signal at an x-coil of the electromagnetic sensor, receiving and measuring a second response signal derived from the first excitation signal at a y-coil, processing the first and second response signals to determine at least one azimuthal characteristic of the second pipe.

The aforementioned embodiment may have one or more of the following additional elements in any combination: Element 1: further comprising transmitting the at least one excitation signal as a first excitation signal from a first x-coil of the electromagnetic sensor, receiving and measuring the first response signal at the first x-coil or a second x-coil of the electromagnetic sensor, transmitting a second excitation signal from a first y-coil of the electromagnetic sensor, and receiving and measuring a third response signal derived from the second excitation signal at the first y-coil or a second y-coil of the electromagnetic sensor. Element 2: further comprising transmitting the first and second excitation signals at the same frequency. Element 3: further comprising transmitting the first and second excitation signals as a rectangular pulse signal or a sinusoidal pulse signal. Element 4: wherein the first x-coil and the first y-coil comprise a first antenna and the second x-coil and the second y-coil comprise a second antenna, and wherein the first and second antennas are collocated. Element 5: further comprising transmitting the at least one excitation signal from at least one of a first x-coil, a first y-coil, and a z-coil, each of the electromagnetic sensor, receiving and measuring the first response signal by at least one of the first x-coil, the first y-coil, a second x-coil of the electromagnetic sensor, and a second y-coil of the electromagnetic sensor, and processing the first response signal to determine the at least one azimuthal characteristic of the second pipe. Element 6: wherein transmitting the at least one excitation signal comprises transmitting at least two excitation signals, the method further comprising transmitting the at least two excitation signals at the same frequency. Element 7: further comprising transmitting the at least two excitation signals as a rectangular pulse signal or a sinusoidal pulse signal. Element 8: wherein processing the response signal comprises comparing the response signal to modeled signals from a computer model, the computer model being created as a function of one or more characteristics of the second pipe, undertaking a numerical inversion of the response signal in view of the modeled signals, and selecting the azimuthal characteristic based on a pipe characteristic of the one or more characteristics of the second pipe that produces a smallest difference between the modeled signals and the response signal. Element 9: wherein the first x-coil, the first y-coil, and the z-coil comprise a first antenna and the second x-coil and the second y-coil comprise a second antenna, and wherein the first and second antennas are collocated. Element 10: further comprising transmitting the at least one excitation signal as a first excitation signal from each of a first x-coil, a first y-coil, and a first z-coil, each of the electromagnetic sensor, receiving and measuring the first response signal derived from the first excitation signals by at least one of a second x-coil and a second y-coil, each of the electromagnetic sensor, transmitting a second excitation signal from one of a third x-coil, a third y-coil, and a second z-coil, each of the electromagnetic sensor, receiving and measuring a third response signal derived from the second excitation signal by at least one of a fourth x-coil and a fourth y-coil, each of the electromagnetic sensor, and processing the first and third response signals to determine azimuthal characteristics of the first and second pipes. Element 11: wherein the first x-coil, the first y-coil, and the first z-coil comprise a first antenna, the second x-coil and the second y-coil comprise a second antenna, the third x-coil, the third y-coil, and the second x-coil comprise a third antenna, and the fourth x-coil and the fourth y-coil comprise a fourth antenna, and wherein an axial separation distance between the third and fourth antennas is greater than an axial separation distance between the first and second antennas. Element 12: wherein the first and second antennas are collocated and the third and fourth antennas are collocated. Element 13: further comprising transmitting the first and second excitation signals at the same frequency. Element 14: further comprising transmitting the first and second excitation signals as a rectangular pulse signal or a sinusoidal pulse signal. Element 15: further comprising transmitting the at least one excitation signal from a z-coil of the electromagnetic sensor, receiving and measuring the first response signal derived from the at least one excitation signal by at least one of an x-coil and a y-coil, each of the electromagnetic sensor, calculating a defect angle based on the response signal received by the at least one of the x-coil and the y-coil, and plotting the defect angle as a log. Element 16: wherein the x-coil, the y-coil, and the z-coil are collocated. Element 17: wherein the x-coil, the y-coil, and the z-coil are staggered. Element 18: further comprising transmitting the at least one excitation signal from one of a first x-coil, a first y-coil, or a first z-coil, each of the electromagnetic sensor, receiving and measuring the first response signal derived from the at least one excitation signal by at least one of the first x-coil, the first y-coil, a second x-coil of the electromagnetic sensor, and a second y-coil of the electromagnetic sensor, synthesizing the first response signals to an antenna oriented at a selected azimuth angle with respect to the wellbore and thereby obtaining synthesized response signals, and generating a two-dimensional (2D) image of the synthesized response signals by looping over a set of azimuth angles, where a first dimension of the 2D image represents axial position along the wellbore and a second dimension of the 2D image represents azimuth angle. Element 19: wherein synthesizing the response signals comprises synthesizing the response signals that correspond to different rotation angles of the pipe inspection tool, and calculating the synthesized response signals as a function of azimuth angle and depth within the wellbore. Element 20: further comprising transmitting the at least one excitation signal from one of a first x-coil, a first y-coil, or a first z-coil, each of the electromagnetic sensor, receiving and measuring the first response signal derived from the at least one excitation signal by at least one of the first x-coil, the first y-coil, a second x-coil of the electromagnetic sensor, and a second y-coil of the electromagnetic sensor, employing a non-azimuthal pipe model at a selected azimuth angle within the wellbore to calculate a thickness of at least one of the first and second pipes, and generating a two-dimensional (2D) image of the thickness of the at least one of the first and second pipes response signals by looping over a set of azimuth angles, where a first dimension of the 2D image represents axial position along the wellbore and a second dimension of the 2D image represents azimuth angle. Element 21: wherein the non-azimuthal pipe model is a piecewise constant thickness model that varies as a function of azimuth angle.

By way of non-limiting example, exemplary combinations applicable to A, B, and C include: Element 1 with Element 2; Element 1 with Element 3; Element 1 with Element 4; Element 5 with Element 6; Element 6 with Element 7; Element 5 with Element 8; Element 5 with Element 9; Element 10 with Element 11; Element 11 with Element 12; Element 10 with Element 13; Element 10 with Element 14; Element 15 with Element 16; Element 15 with Element 17; Element 18 with Element 19; and Element 20 with Element 21.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A method, comprising:
conveying a pipe inspection tool into a wellbore having at least a first pipe positioned within a second pipe, the pipe inspection tool including an electromagnetic sensor;
transmitting a first excitation signal from a first x-coil of the electromagnetic sensor;
receiving and measuring a first response signal derived from the first excitation signal at the first x-coil or a second x-coil of the electromagnetic sensor;
transmitting a second excitation signal from a first y-coil of the electromagnetic sensor;
receiving and measuring a second response signal derived from the first second excitation signal at the first y-coil or a second y-coil of the electromagnetic sensor; and
processing the first and second response signals to determine at least one azimuthal characteristic of the second pipe, wherein the first x-coil and the first y-coil comprise a first antenna and the second x-coil and the second y-coil comprise a second antenna, and wherein the first and second antennas are collocated.

2. The method of claim 1, further comprising transmitting the first and second excitation signals at the same frequency.

3. The method of claim 1, further comprising transmitting the first and second excitation signals as a rectangular pulse signal or a sinusoidal pulse signal.

4. A method, comprising:
conveying a pipe inspection tool into a wellbore having at least a first pipe positioned within a second pipe, the pipe inspection tool including an electromagnetic sensor;
transmitting an excitation signal from at least one of a first x-coil of the electromagnetic sensor, a first y-coil of the electromagnetic sensor, and a z-coil of the electromagnetic sensor;
receiving and measuring a response signal derived from the excitation signal by at least one of the first x-coil, the first y-coil, a second x-coil of the electromagnetic sensor, and a second y-coil of the electromagnetic sensor; and
processing the response signal to determine an azimuthal characteristic of the second pipe, wherein the first x-coil, the first v-coil, and the z-coil comprise a first antenna and the second x-coil and the second y-coil comprise a second antenna, and wherein the first and second antennas are collocated.

5. The method of claim 4, wherein transmitting the excitation signal comprises transmitting at least two excitation signals, the method further comprising transmitting the at least two excitation signals at the same frequency.

6. The method of claim 5, further comprising transmitting the at least two excitation signals as a rectangular pulse signal or a sinusoidal pulse signal.

7. The method of claim 4, wherein processing the response signal comprises:
comparing the response signal to modeled signals from a computer model, the computer model being created as a function of one or more characteristics of the second pipe;
undertaking a numerical inversion of the response signal in view of the modeled signals; and
selecting the azimuthal characteristic based on a pipe characteristic of the one or more characteristics of the second pipe that produces a smallest difference between the modeled signals and the response signal.

8. A method, comprising:
conveying a pipe inspection tool into a wellbore having at least a first pipe positioned within a second pipe, the pipe inspection tool including an electromagnetic sensor;
transmitting a first excitation signal from each of a first x-coil of the electromagnetic sensor, a first y-coil of the electromagnetic sensor, and a first z-coil of the electromagnetic sensor;
receiving and measuring a first response signal derived from the first excitation signals by at least one of a second x-coil of the electromagnetic sensor and a second y-coil of the electromagnetic sensor;
transmitting a second excitation signal from one of a third x-coil of the electromagnetic sensor, a third y-coil of the electromagnetic sensor, and a second z-coil of the electromagnetic sensor;
receiving and measuring a second response signal derived from the second excitation signal by at least one of a fourth x-coil of the electromagnetic sensor and a fourth y-coil of the electromagnetic sensor; and
processing the first and second response signals to determine azimuthal characteristics of the first and second pipes.

9. The method of claim 8, wherein the first x-coil, the first y-coil, and the first z-coil comprise a first antenna, the second x-coil and the second y-coil comprise a second antenna, the third x-coil, the third y-coil, and the second z-coil comprise a third antenna, and the fourth x-coil and the fourth y-coil comprise a fourth antenna, and wherein an axial separation distance between the third and fourth antennas is greater than an axial separation distance between the first and second antennas.

10. The method of claim 9, wherein the first and second antennas are collocated and the third and fourth antennas are collocated.

11. The method of claim 8, further comprising transmitting the first and second excitation signals at the same frequency.

12. The method of claim 8, further comprising transmitting the first and second excitation signals as a rectangular pulse signal or a sinusoidal pulse signal.

13. A method, comprising:
conveying a pipe inspection tool into a wellbore having at least a first pipe positioned within a second pipe, the pipe inspection tool including an electromagnetic sensor;
transmitting an excitation signal from a z-coil of the electromagnetic sensor;
receiving and measuring a response signal derived from the excitation signal by at least one of an x-coil of the electromagnetic sensor and a y-coil of the electromagnetic sensor, wherein the x-coil, the y-coil, and the z-coil are collocated;
calculating a defect angle based on the response signal received by the at least one of the x-coil and the y-coil; and
plotting the defect angle as a log.

14. A method, comprising:
conveying a pipe inspection tool into a wellbore having at least a first pipe positioned within a second pipe, the pipe inspection tool including an electromagnetic sensor;
transmitting an excitation signal from one of a first x-coil of the electromagnetic sensor, a first y-coil of the electromagnetic sensor, or a first z-coil of the electromagnetic sensor;

receiving and measuring a response signal derived from the excitation signal by at least one of the first x-coil, the first y-coil, a second x-coil of the electromagnetic sensor, and a second y-coil of the electromagnetic sensor;

synthesizing the response signals to an antenna included in the pipe inspection tool and oriented at a selected azimuth angle with respect to the wellbore and thereby obtaining synthesized response signals; and generating a two-dimensional (2D) image of the synthesized response signals by looping over a set of azimuth angles, where a first dimension of the 2D image represents axial position along the wellbore and a second dimension of the 2D image represents azimuth angle.

15. The method of claim 14, wherein synthesizing the response signals comprises:

synthesizing the response signals that correspond to different rotation angles of the pipe inspection tool; and calculating the synthesized response signals as a function of azimuth angle and depth within the wellbore.

16. A method, comprising:

conveying a pipe inspection tool into a wellbore having at least a first pipe positioned within a second pipe, the pipe inspection tool including an electromagnetic sensor;

transmitting an excitation signal from one of a first x-coil of the electromagnetic sensor, a first y-coil of the electromagnetic sensor, or a first z-coil of the electromagnetic sensor;

receiving and measuring a response signal derived from the excitation signal by at least one of the first x-coil, the first y-coil, a second x-coil of the electromagnetic sensor, and a second y-coil of the electromagnetic sensor;

employing a non-azimuthal pipe model at a selected azimuth angle within the wellbore to calculate a thickness of at least one of the first and second pipes; and generating a two-dimensional (2D) image of the thickness of the at least one of the first and second pipes by looping over a set of azimuth angles, where a first dimension of the 2D image represents axial position along the wellbore and a second dimension of the 2D image represents azimuth angle.

17. The method of claim 16, wherein the non-azimuthal pipe model is a piecewise constant thickness model that varies as a function of azimuth angle.

* * * * *